United States Patent
Chenchik et al.

(12)

(10) Patent No.: US 10,196,634 B2
(45) Date of Patent: Feb. 5, 2019

(54) CLONAL ANALYSIS OF FUNCTIONAL GENOMIC ASSAYS AND COMPOSITIONS FOR PRACTICING SAME

(71) Applicant: Cellecta, Inc., Mountain View, CA (US)

(72) Inventors: Alex Chenchik, Redwood City, CA (US); Donato Tedesco, Berkeley, CA (US); Mikhail Makhanov, San Francisco, CA (US)

(73) Assignee: Cellecta, Inc., Mountain View, CA (US)

( * ) Notice: Subject to any disclaimer, the term of this patent is extended or adjusted under 35 U.S.C. 154(b) by 150 days.

(21) Appl. No.: 15/174,634

(22) Filed: Jun. 6, 2016

(65) Prior Publication Data

US 2016/0340671 A1    Nov. 24, 2016

Related U.S. Application Data

(62) Division of application No. 13/890,017, filed on May 8, 2013, now Pat. No. 9,429,565.

(Continued)

(51) Int. Cl.
  *C12N 15/113* (2010.01)
  *C12N 15/10* (2006.01)
  *G01N 33/50* (2006.01)

(52) U.S. Cl.
  CPC ..... *C12N 15/1082* (2013.01); *C12N 15/1034* (2013.01); *C12N 15/1065* (2013.01);
  (Continued)

(58) Field of Classification Search
  CPC .................................. C12N 15/1082
  (Continued)

(56) References Cited

U.S. PATENT DOCUMENTS

2007/0202505 A1    8/2007  Chenchik
2010/0305002 A1    12/2010 Chenchik et al.

FOREIGN PATENT DOCUMENTS

EP        2208785 A1    7/2010
WO    WO2004029219 A2    4/2004
(Continued)

OTHER PUBLICATIONS

Paddison et al.'s Supplementary Methods, Nature, Mar. 25, 2004, pp. 1-11 (Year: 2004).*

(Continued)

*Primary Examiner* — Karla A Dines
(74) *Attorney, Agent, or Firm* — Bret E. Field; Bozicevic, Field & Francis LLP

(57) ABSTRACT

Methods of clonal analysis of functional genomic assays are provided. Aspects of the invention include transducing a population of target cells with a packaged viral effector library made up of a plurality of effector construct subsets, wherein each effector construct subset of the library includes a plurality of effector constructs having a common effector cassette linked to a distinct clonal barcode. Inclusion of distinct clonal barcodes in the effector construct subset allows for determination of the clonal representation of an effector construct subset in transduced target cells that exhibit a specific phenotype. Aspects of the invention further include compositions, e.g., libraries and components thereof, which find use in practicing the methods.

21 Claims, 13 Drawing Sheets

Specification includes a Sequence Listing.

Related U.S. Application Data

(60) Provisional application No. 61/644,324, filed on May 8, 2012.

(52) U.S. Cl.
CPC ..... *C12N 15/1075* (2013.01); *C12N 15/1079* (2013.01); *C12N 15/113* (2013.01); *G01N 33/5008* (2013.01); *C12N 2310/14* (2013.01); *C12N 2310/531* (2013.01); *C12N 2330/31* (2013.01)

(58) Field of Classification Search
USPC ...................................................... 506/14, 17
See application file for complete search history.

(56) References Cited

FOREIGN PATENT DOCUMENTS

| WO | WO2005026378 A1 | 3/2005 |
|----|-----------------|--------|
| WO | WO2007133710 A2 | 11/2007 |
| WO | WO2009112844 A2 | 9/2009 |
| WO | WO2010129310 A1 | 11/2010 |

OTHER PUBLICATIONS

Paddison et al., A resource for large-scale RNA-interference-based screens in mammals, Nature. Mar. 25, 2004;428 (6981):427-31.
Jager et al., In Vivo Screening for Tumor Suppressors In Hematological Malignancies Using Barcode RNAi, Blood, 52th Annual Meeting for American-Society-of-Hematology (ASH), 2010 116(21): Abstract 998.
Bernards et al., "shRNA libraries and their use in cancer genetics", Nature Methods, vol. 3, No. 9, pp. 701-706 (2006).
Boettcher et al., "Decoding pooled RNAi screens by means of barcode tiling arrays", BMC Genomics, vol. 11, Article No. 7, pp. 1-16 (2010).
Cheung et al., Systematic investigation of genetic vulnerabilities across cancer cell lines reveals lineage-specific dependencies in ovarian cancer, Proc Natl Arad Sci U S A (2011),108(30):12372-12377.
Fewell et al., "Vector-based RNAi approaches for stable, inducible and genome-wide screens", Drug Discovery Today, vol. 11, Nos. 21/22, pp. 975-982 (2006).
Gerrits et al., "Cellular barcoding tool for clonal analysis in the hematopoietic system", Blood, vol. 115, No. 13, pp. 2610-2618 (2010).
Gresham et al., "System-Level Analysis of Genes and Functions Affecting Survival During Nutrient Starvation in *Saccharomyces cerevisiae*", Genetics, vol. 187, pp. 299-317 (2011).
Hamady et al., "Error-correcting barcoded primers for pyrosequencing hundreds of samples in multiplex", Nature Mehods, vol. 5, No. 3, pp. 235-237 (2008).
http://www.cellecta.com ("CELLECTA" Webpage) Mar. 2012 (tracked by online Wayback Machine) See Products Services page(RNAi genetic screens), and Technology page (shRNA library construction, and RNAi genetic screening.
Mazurkiewicz et al., "Signature-tagged mutagenesis: barcoding mutants for genome-wide screens", Genetics, vol. 7, pp. 929-939 (2006).
Mendes-Pereira et al., Genome-wide functional screen identifies a compendium of genes affecting sensitivity to tamoxifen, Proc Natl Arad Sci U S A (2012),109(8): 2730-2735.
Moffat et al., A lentiviral RNAi library for human and mouse genes applied to an arrayed viral high-content screen, Cell (2006), 124(6):1283-1298.
Nolan-Stevaux et al., "Measurement of Cancer Cell Growth Heterogeneity through Lentiviral Barcoding Identifies Clonal Dominance as a Characteristic of In Vivo Tumor Engraftment", PLOS ONE, vol. 8, No. 6, pp. e67316-e67316 (2013).
Pierce et al., "Genome-wide analysis of barcoded *Saccharomyces cerevisiae* gene-deletion mutants in pooled cultures", Nature Protocols, vol. 2, No. 11, pp. 2958-2974 (2007).
Sandmann et al., Screens, maps & networks: from genome sequences to personalized medicine, Curr Opin Genet Dev (2012),22(1):36-44.
Schlabach et al., Cancer proliferation gene discovery through functional genomics, Science (2008), 319 (5863):620-624.
Shtutman et al., "Function-based gene identification using enzymatically generated normalized shRNA library and massive parallel sequencing", PNAS, vol. 107, No. 16, pp. 7377-7382 (2010).
Silva et al., Profiling Essential Genes in Human Mammary Cells by Multiplex RNAi Screening, Science (2008), 319 (5863):617-620.
Sims et al., "High-throughput RNA interference screening using pooled shRNA libraries and next generation sequencing", Genome Biology, vol. 12, Article No. R104, pp. 1-13 (2011).
Smith et al., "Competitive Genomic Screens of Barcoded Yeast Libraries", Journal of Visualized Experiments, vol. 54, No. e2864, pp. 1-7 (2011).
Warner et al., "Rapid profiling of a microbial genome using mixtures of barcoded oligonucleotides", Nature Biotechnology, vol. 28, No. 8, pp. 856-862 (2010).

\* cited by examiner

FIG. 5A

Fwdbc1 SEQ ID NO:1
AACGACTAACGATGTCTCGACC    Bpil    Bpil    14n Barcode    BsmBI
SEQ ID NO:2 ATGGTC[...]AGTCTG[...]TTTT[NNNNNNNNNNNNNN][...]
                BsmBI                                      RevBC1
                                         SEQ ID NO:3 AAGCACTCCGCACATAGCAACCA

FIG. 5B

U6 promoter
SEQ ID NO:4   [U6—...]
SEQ ID NO:5   [U6—...]
              Bpil                  Bpil
                                                          EcoRI       cPPT
              [...]TCCGACTGTAGAACTCTGAACCTGAGCGCCTCGGTGTCCAGCCACCGAGCCCAGAGCTGAGCATTAGAATTCGAAT...CGAACCTGAGCGCCTCGGTGGTTACGGT...

FIG. 5C

SEQ ID NO:6 Fwd-U6-1           SEQ ID NO:7    GexMS-U6-1
ACAAGCTGTTAGAAGATAATTGGA       CAACCAGAAGACGGCATACGAGATTAGTACAAAATACTTGACGTAGAA
                                                                                    EcoRI   cPPT
SEQ ID NO:9                                                                                 Rev-cPPT5
SEQ ID NO:8  [...]TCCGACTGTAGAACTCTGAACCTGAGCGCCTCGGTGGTCCAGCCACCGAGCCCTATCATTAGAATTCTGACCTGAGCGCCTCGGTGGAGCCTCGTGTTACCGT
              Bpil                                                GexSeqM    AGAGCCACCACGGGATAGTAA   SEQ ID NO:11
              SEQ ID NO:10 AAGCCTGACATGACATTGAGACTTGAGAGA         SEQ ID NO:12 GexZM

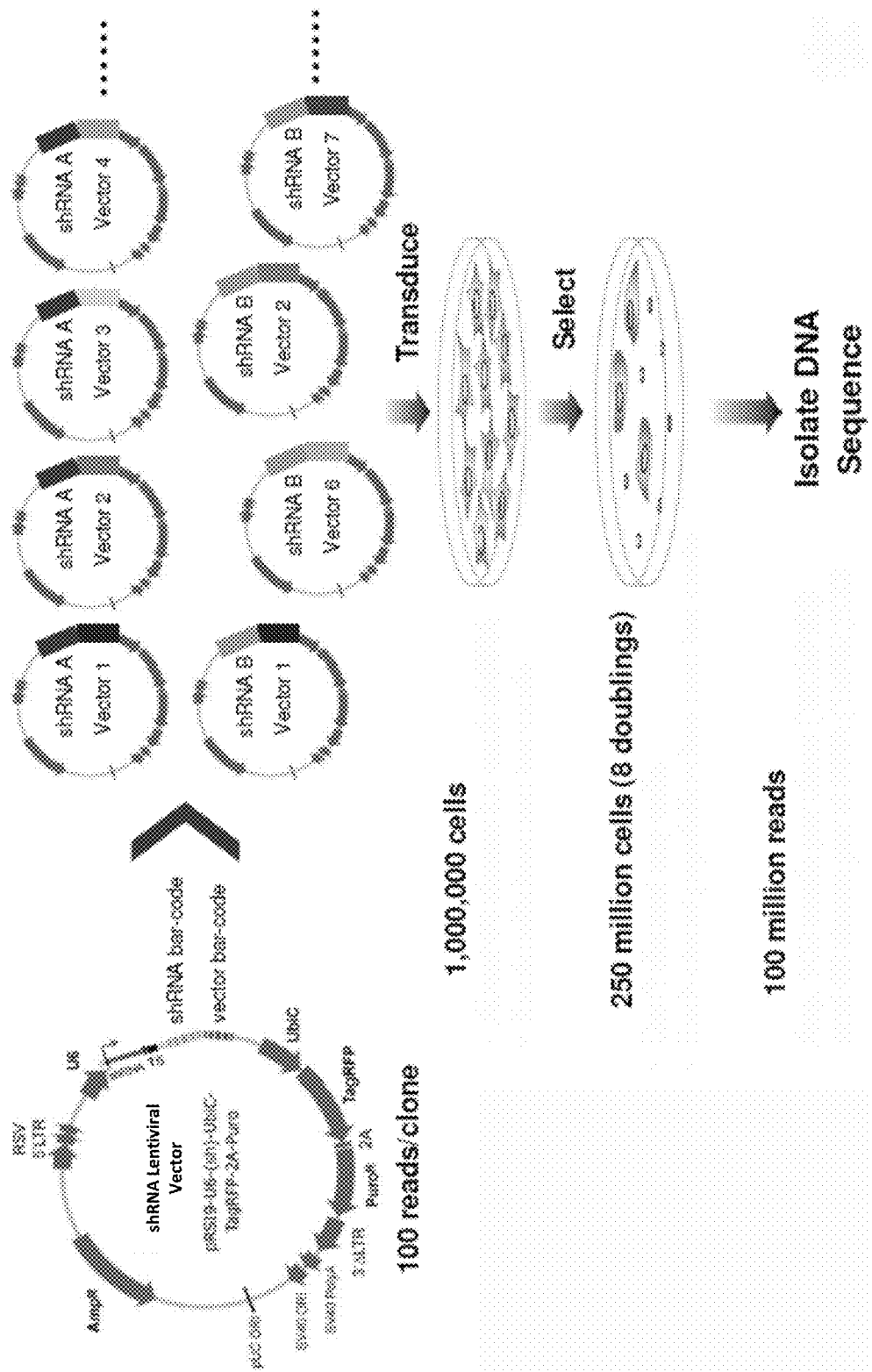

FIG. 9F
(i)
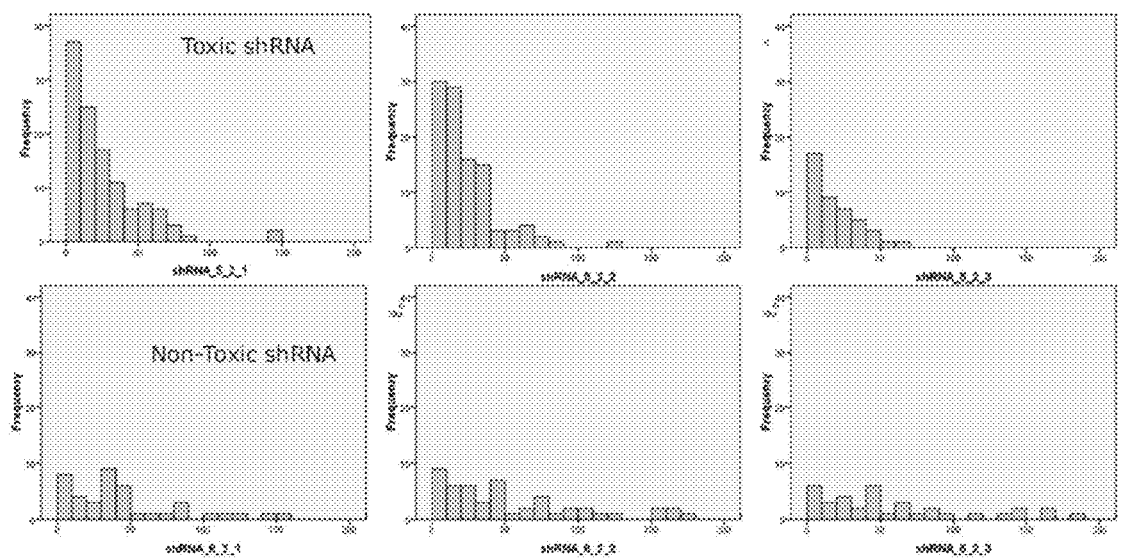
(ii)
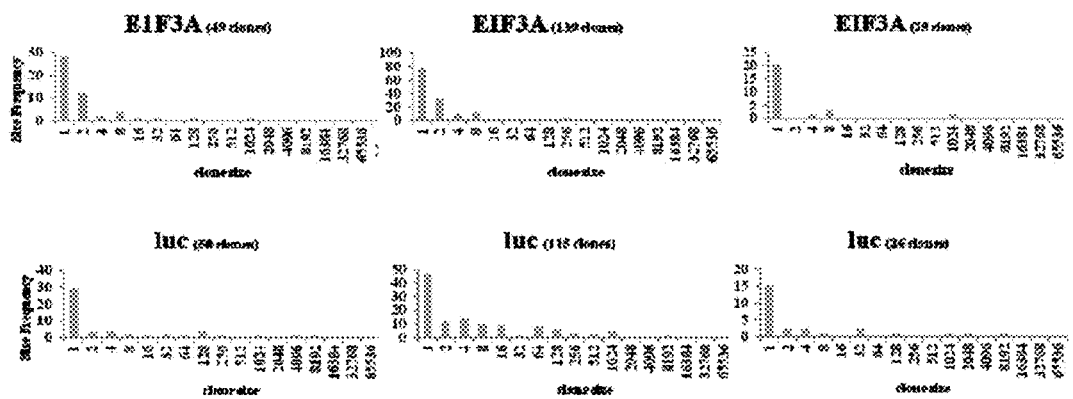

CLONAL ANALYSIS OF FUNCTIONAL GENOMIC ASSAYS AND COMPOSITIONS FOR PRACTICING SAME

CROSS-REFERENCE TO RELATED APPLICATION

Pursuant to 35 U.S.C. § 119(e), this application claims priority to U.S. Provisional Application Ser. No. 61/644,324 filed on May 8, 2012, the disclosure of which is herein incorporated by reference.

INTRODUCTION

As a result of various genome-wide sequencing projects such as the Human Genome Project, researchers now know the sequence of many human genes. However, there is an urgent need to develop tools to uncover the function(s) of each of these genes. Importantly, functional genomic assays will speed up the discovery and validation of drug targets.

Several technologies have been developed for studying the function of genes, where such studies may be collectively referred to as functional genomic assays and are based on the selective inactivation or activation of gene products, both in vitro and in vivo. Effectors that can be used to target gene products include, but are not limited to: catalytic RNAs, such as antisense RNAs, ribozymes, maxizymes and aptazymes (see, e.g., Kuwabara, T. et al., Trends Biotechnol., 18:462-468 (2000); and Famulok, M., and Verma, S., Trends Biotechnol., 20 462-468 (2002)); protein-binding RNA motifs such as aptamers and intramers (again, see, e.g., Kuwabara, T. et al., Trends Biotechnol., 18:462-468 (2000)), and genetic suppressor elements, based on bioactive peptides, protein domains or anti-sense RNAs (see, e.g., Robinson, I. B., and Gudkov, A. V, Methods in Molecular Biology, Tumor Suppressor Genes: Pathways and Isolation Strategies (Ed. Wafik, S. E.) Humana Press Inc., 222:411-434 (2002)). Moreover, expression of full-length proteins expressed from and delivered by genetic constructs has proven to be a very effective gain-of-function strategy to study gene function in cells.

RNAi is the sequence-specific, post-transcriptional silencing of a gene's expression by double-stranded RNA. RNAi is mediated by 21- to 25-nucleotide, double-stranded RNA molecules referred to as small interfering RNAs (siRNAs). siRNAs can be derived by enzymatic cleavage of double-stranded precursor short interfering RNAs (shRNA) expressed from genetic constructs or micro RNA precursors in cells. siRNAs also can also be synthesized chemically or enzymatically outside of cells and subsequently delivered to cells (see, for example, Fire, et al., Nature, 391:806-11 (1998); Tuschl, et al., Genes and Dev., 13:3191-97 (1999); and Elbashir, et al., Nature, 411:494-498 (2001)).

Double stranded siRNAs mediate gene silencing by targeting for disruption, cleaving, or blocking the synthesis, processing or translation of messenger RNAs (mRNAs) that contain a sequence at least partially complementary to one strand of the siRNA. Short (19-29 nucleotide length) siRNAs introduced into mammalian cells mediate sequence-specific gene silencing, whereas long, double-stranded RNAs (more than about 30 nucleotides), in addition to gene silencing, have been shown to induce non-specific responses, such as interferon response.

Thus, siRNA can be used for selective inactivation (silencing) of gene products. The typical approach in using siRNA is to study the effect of various siRNAs on each target gene; that is, to perform a functional screen by inactivating one gene at a time. Several companies (Dharmacon, Qiagen, and Ambion, for example) currently offer custom and pre-made siRNA constructs that can be used in such gene knockdown experiments. In addition, progress has been made to overcome the transient nature of the gene silencing effects of synthetic siRNAs by developing plasmid and viral shRNA or microRNA constructs that provide continuous siRNA expression. These vectors direct the synthesis of fold-back stem-loop transcripts (short hairpin shRNAs) from an RNA polymerase III promoter (U6 or H1) or micro RNA from RNA polymerase II promoters, where the hairpin structure subsequently is converted into a non-hairpin double-stranded siRNA structure after intracellular processing.

RNAi technology can be effectively used to knockdown function(s) of a single gene. Alternatively, a genetic screen approach can be employed to study function of multiple genes based on the delivery of a set of synthetic or genetic constructs each targeting different genes in an arrayed or pooled format. Currently, RNAi gene function analysis studies are mainly limited by the complexity of cell-based phenotypic responses. There is a significant need to develop improved technologies for RNAi gene functional analysis which can address a variety of different cellular responses in a heterogeneous cell population.

SUMMARY

Methods of clonal analysis of functional genomic assays are provided. Aspects of the invention include transducing a population of target cells with a packaged viral effector library made up of a plurality of effector construct subsets, wherein each effector construct subset of the library includes a plurality of effector constructs having a common effector cassette linked to a distinct clonal barcode. Inclusion of distinct clonal barcodes in the effector construct subset allows for determination of the clonal representation of an effector construct subset in transduced target cells that exhibit a specific phenotype. Aspects of the invention further include compositions, e.g., libraries and components thereof, which find use in practicing the methods.

BRIEF DESCRIPTION OF THE FIGURES

FIGS. 5A-5C provide details regarding the construction and design of a 3.2K Clonal Barcode library, as reported in the Experimental Section below.

FIGS. 6A-6C provide details regarding the construction and design of a Clonal 27K Decipher shRNA Library, as reported in the Experimental Section below.

FIGS. 9A to 9J provide additional details regarding aspects of an embodiment of the invention.

DEFINITIONS

Figure 1:
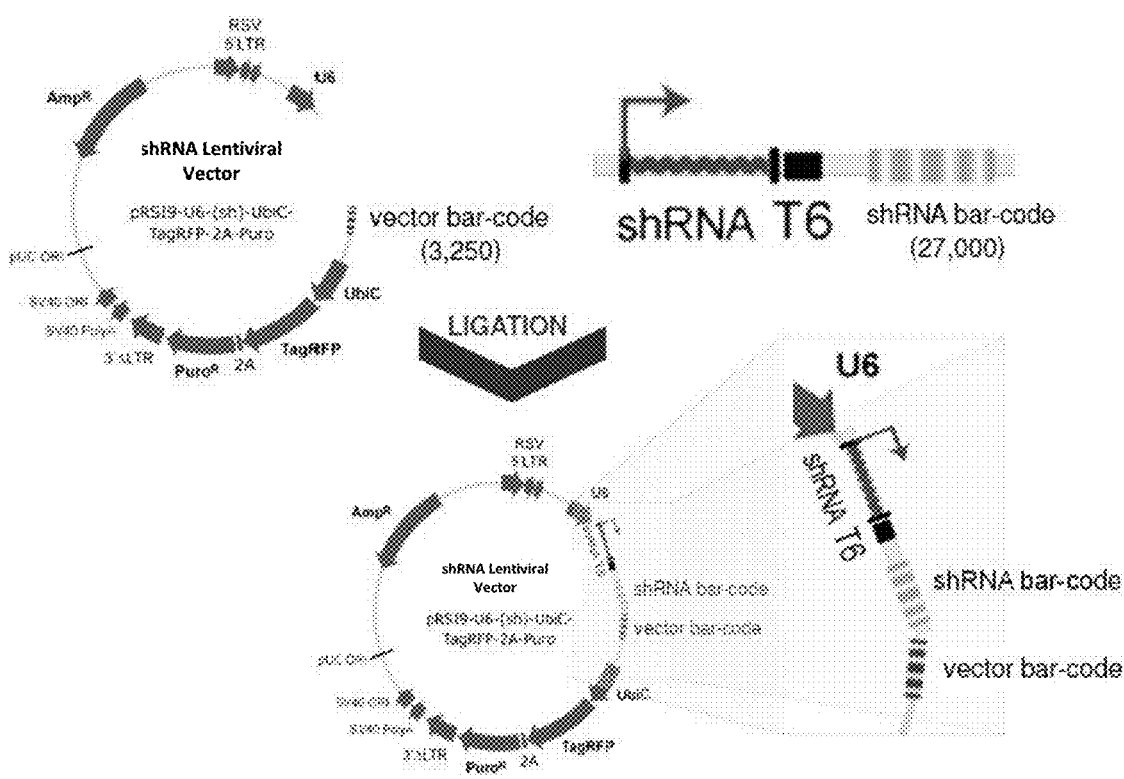
FIG. 1 illustrates a protocol for generating a RNAi effector library according to an embodiment of the invention.

The term "vector" is used in its conventional sense to refer to a DNA molecule used as a vehicle to clone and transfer foreign genetic material, e.g., an effector construct, into a cell. Examples of vectors include plasmids, viruses, cosmids and artificial chromosomes. Vectors finding use in embodiments of the invention may be employed in linear or circular form and may be either RNA or DNA, and may be either single- or double-stranded form, as desired.

The term "effector" is used to refer to a biochemical molecule that can affect the transcription, translation, expression, processing or function of another molecule or molecules, such as a target gene or the product of a target gene. Effectors may be full-length proteins, protein domains, peptides, single-stranded or double-stranded deoxy- or ribo-oligonucleotides, shRNAs, siRNAs, micro RNAs, regulatory RNAs including small RNAs and non-coding RNAs, or mimetics or analogues thereof.

The term "effector construct" is used to refer to nucleic acid construct that includes an effector cassette linked to a clonal barcode and a vector domain. Effector cassettes of interest include at least an effector sequence, where the effector sequence may be operationally-linked to a promoter, e.g., for expression of the effector sequence in a cell that includes the effector construct. Optionally, an effector cassette may include an effector-specific barcode, e.g., to facilitate identification of effector sequence. In addition, an effector construct may include one or more markers, e.g., a reporter or drug-resistance gene, under control of promoter for selection or labeling of cells expressing effector construct. As described in greater detail below, effector libraries employed in methods of the invention may include effector construct subsets made of a plurality, i.e., pool, of different effector constructs sharing a common effector cassette but a different clonal barcode.

A "promoter sequence" (also referred to herein as a promoter) is a DNA regulatory region capable of binding RNA polymerase in a cell and initiating transcription of a coding sequence. For example, the promoter sequence may be bounded at its 3' terminus by the transcription initiation site and extend upstream (in the 5' direction) to include the minimum number of bases or elements necessary to initiate transcription at levels detectable above background. Within the promoter sequence may be found a transcription initiation site, as well as protein binding domains responsible for the binding of RNA polymerase or other transcriptional factors. Eukaryotic promoters will often, but not always, contain "TATA" boxes and "CAT" boxes. Various promoters, such as those recognized by RNA polymerase II or RNA polymerase III and/or inducible promoters known in the art may be used to drive the various vectors of the present invention.

The terms "restriction endonucleases" or "restriction enzymes" refer generally to bacterial enzymes that cut double-stranded DNA at or near a specific nucleotide sequence.

A cell has been "transformed", "transduced" or "transfected" by an effector construct or effector library when such genetic construct (s) has been introduced inside the cell, for example, as a complex with transfection reagents or packaged in viral particles. The transforming effector construct may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a host cell chromosome or is maintained extra-chromosomally so that the transforming DNA is inherited by daughter cells during cell replication. In some instances, the transformed cells acquire single effector construct transduced in the target cell by genetic construct packaged in pseudoviral particle. Such a stably transduced eukaryotic cell is able to establish cell lines or clones comprised of a population of daughter cells containing the effector construct and labeled with the clonal barcode specific for that clone.

The term "small interfering RNA" or "siRNA" refers generally to substantially double-stranded RNA molecules that inhibit the expression of a gene with which they share homology.

The term "microarray" refers to arrays or ordered arrangements of different targets, such as proteins, peptides or nucleic acids on a solid or semi-solid support such as a slide, membrane, chip, bead, or microwell plate with a known location or address of each target. Targets can be bound to a support by photolithographic techniques, phosphoramidite chemistry, photochemistry, electrochemistry, covalent or non-covalent immobilization or other methods known in the art.

The term "effector library" refers to the set of at least two or more effector constructs. Effector libraries of interest can be employed in genetic screens, e.g., in a pooled or an arrayed format. In the pooled format the effector constructs may be mixed together and present in the effector library at similar abundance level. In the arrayed format the effector constructs may be transduced in the target cells separately.

DETAILED DESCRIPTION

Methods of clonal analysis of functional genomic assays are provided. Aspects of the invention include transducing a population of target cells with a packaged viral effector library made up of a plurality of effector construct subsets, wherein each effector construct subset of the library includes a plurality of effector constructs having a common effector cassette linked to a distinct clonal barcode. Inclusion of distinct clonal barcodes in the effector construct subset allows for determination of the clonal representation of an effector construct subset in transduced target cells that exhibit a specific phenotype. Aspects of the invention further include compositions, e.g., libraries and components thereof, which find use in practicing the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to ante-date such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, methods of functional genomic assays that include clonal analysis of target cells transduced with effector constructs or effector libraries thereof are provided. By "clonal analysis" is meant that the functional genomic assay results are evaluated with respect to both: (a) total cellular populations exhibiting phenotypic changes or characteristics (e.g., growth rate, induction of apoptosis, differentiation, changes in cell cycle, modulation of specific signaling pathway, expression of specific marker, etc.) of interest and arise from a specific effector molecule; and (b) individual clonal populations of the total cellular populations that exhibit an specific effector construct. In other words, the total population of cells of interest that express the same effector are not considered equal—instead such total populations are analyzed to identify differences among the distinct clonal populations making up the total population, where differences in the clonal population (e.g., in terms of number of cells in each clonal population) may be attributed to the expression of the effector. For example, where the functional genomic assay is a viability screen (e.g., where the phenotypic change of interest may a change in the suppression or growth of cells), the number of cells in each clonal population exhibiting the phenotype of interest may be determined to identify differences in different clonal cell population numbers. In the case of a genetic screen of a complex effector library, the transduced target cells may first be grouped according to the presence of each specific effector construct that is present in the effector library and then clonal analysis may be applied for each effector-specific cell population as described above. In another strategy for a genetic screen with an effector library, the cells exhibiting the characteristic of interest are isolated and analyzed based on the number of clones for the each specific effector construct. Accordingly, for a given observed characteristic of interest in the genetic screen, two or more clonal populations that exhibit the characteristic of interest may be distinguished from each other. Where multiple distinct clonal populations are identified has having a common characteristic of interest arising from the same effector, these multiple clonal populations may be identified either qualitatively or quantitatively. As such, one can readily determine via methods of the invention, the number of distinct clonal populations (i.e., clonal populations arising from different initial transduced target cells) in which an effector is giving rise to characteristic of interest, and therefore the number of different initial target cells that were transduced with an effector giving rise to the characteristic of interest. One can also readily determine the number of cells in a given identified clonal population, so as to make a quantitative clonal analysis of the genetic screen. As such, practice of the methods of the invention provides information on the total number of distinct clonal populations, and therefore distinct cellular precursors (i.e., transduced target cells), that exhibit a characteristic of interest. For example, if 10 clonal populations having a common effector exhibit a characteristic of interest in an effector library screen, methods of the invention provide information that 10 different clonal populations, and therefore 10 different source cells, exhibit the characteristic of interest. In addition, the 10 different clonal populations and therefore 10 different precursor cells in such an instance may be readily distinguished from each other. Furthermore, the total number of cells from in each of the identified clonal populations may be determined. The resultant clonal analysis data of the functional genomic assay, i.e., genetic screen, may be used for a variety of different purposes, e.g., as described in greater detail below.

A variety of different effector constructs or effector libraries thereof can be employed in genetic screens and clonally analyzed in accordance with embodiments of the invention. As indicated above, by "functional genomic assay" or "genetic screen" is meant any procedure in which the activity of single effector or members a library of effectors is evaluated. Effectors (e.g., compounds referred to a small molecules) that are screened may vary widely, e.g., as described above. In certain embodiments, effectors that are screened are those that are biopolymeric, where the effectors may be encoded by nucleic acids and expressed in the cells from operationally-linked promoter, e.g., as described in greater detail below. Effectors of interest include, but are not limited to: nucleic acid effectors, e.g., ribonucleic acid effectors, such as RNAi effectors (e.g., siRNA, shRNA, microRNA), ribozymes, etc.; deoxyribonucleic acid effectors, such as antisense; peptide and protein effectors, such as bioactive peptides, protein domains or full-length (ORF) proteins; etc.

Effectors which may be evaluated in methods of the invention include those that are present in an effector construct subset of an effector library. An effector construct subset is a plurality of or pooled collection of nucleic acids that have the same effector nucleic acid sequence but different clonal barcodes, where these components are described in greater detail below. As such, in a given subset, the effector constructs are ones that share a common effector nucleic acid, i.e., the effector nucleic acid of the constructs has the same sequence, but differ from each other in terms of clonal barcode, i.e., the clonal barcodes among different members of the subset have differing sequences. The number of distinct clonal barcodes, i.e., those having a different sequence, which is present in a given subset may be 10 or more, such as 100 or more and including 1,000 or more. In other words, the effector construct subsets employed in embodiments of the invention are, in some instances, mixtures (i.e., sublibraries) of 10 or more nucleic acid constructs encoding the same effector and one of a plurality (e.g., 10 or more) distinct clonal barcodes of differing sequence. Effector libraries of interest are those having multiple different effectors of the same type of effector, i.e., multiple different effector construct subsets. Thus, a given effector library may be an RNAi effector library, where each of the effectors in the library will be the same type of RNAi effector, (e.g., shRNA, microRNA, etc.), where the different effectors in the library will differ from each other by sequence. The number of distinct effectors (e.g., of differing sequence) in a given effector library may vary, where in some instances the number is 2 or more, such as 5 or more, such as 100 or more, including 1000 or more, and in certain embodiments 5,000 or more; 10,000 or more; 50,000 or more, etc. Examples of effector libraries of interest include, but are not limited to, those described in: Kassner, Q. K. Expert Opin. Ther. Targets (2009) 13:1027-1035 (describing an RNA interference screen for the discovery of oncology targets); Luo et al., Proc. Natl. Aced. Sci. (2008) 105:20380-20385 (describing parallel identification of essential genes in cancer cells); Zuber et al. Nature Biotechnol. (2011) 29:79-85 (describing the evaluation of genes required for proliferation and survival using tetracycline-regulated RNAi); Schlabach, et al., Science (2008) 319(5863):620-4. Erratum in: Science. 2008 Apr. 18; 320(5874):316 (describing a functional genomics approach to the discovery of cancer proliferation genes); Silva et al., Science (2008) 319(5863):617-20 (describing the profiling of essential genes in human mammary cells by multiplex RNAi screening); Ngo et al., Nature (2006) 441: 106-110 (describing a loss-of-function RNAi screen for molecular targets in cancer); Smolen et al. Genes Develop. (2010)24:2654-2665 (describing a genome-wide RNAi screen to identify multiple RSK-dependent regulators of cell migration); Huang et al. BMS Systems Biol. (2008) 2:49-59 (describing a systems analysis of quantitative shRNA-library screens to identify regulators of cell adhesion); Kiefer et al. Methods Mol. Biol. (2009) 563:275-287 (describing high-throughput siRNA screening as a method of perturbing biological systems and identifying targeted pathways coupled with compound screening); Brummelkamp et al. Nat. Chem. Biol. (2006) 2:202-206 (describing an shRNA barcode screen relating to cancer cell vulnerability to MDM2 inhibitors); Ji et al. Oncol. Reports (2007) 18:1499-1505 (describing a screen of shRNAs targeting tumor suppressor genes to identify factors involved in A549 paclitaxel sensitivity); Turner et al. EMBO J. (2008) 27:1368-1377 (describing a synthetic lethal siRNA screen identifying genes that mediate sensitivity to a PARP inhibitor); Azorsa et al. J. Transl. Medicine (2009) 7:43-55 (describing a synthetic lethal RNAi screening to identify targets for gemcitabine therapy in pancreatic cancer); Whitehurst et al. Nature (2007) 446:2815-819 (describing a synthetic lethal screen to identify chemosensitizer loci in cancer cells); Klinghoffer et al. Assay Drug. Devel. Technol. (2008) 6:105-119 (describing an optimized lentivirus-mediated RNAi screen to identify modulators of kinesin-5 inhibitor sensitivity); Wiltshire et al. J. Biol. Chem. (2010) 285:14565-14571 (describing ubiquitin-specific peptidase 11 as a regulator of DNA double-strand break repair via sensitivity to poly(ADP-ribose) polymerase); Gregory et al. Cancer Cell (2010) 18:74-87 (describing that Wnt/Ca2+/NFAT signaling maintains survival of Ph+ leukemia cells upon inhibition of Bcr-Abl); Astsaturov et al. Cancer Biol. (2010) 3:1-17 (describing a synthetic lethal screen of an EGFR-centered network to improve targeted therapies); O'Connell et al. Molecular Cell (2010) 40:645-657 (describing a genome-wide camptothecin sensitivity screen to identify a mammalian MMS22L-NFKBIL2 complex required for genomic stability); Hurov et al. Genes Develop. (2010) 24:1939-1950 (describing a genetic screen to identify the triple T complex required for DNA damage signaling and ATM and ATR stability); Barbie et al. Nature (2009) 462:108-114 (describing a systematic RNA interference approach revealing that oncogenic KRAS-driven cancers require TBK1); Scholl et al. Cell (2009) 137:8210-834 (describing a synthetic lethal interaction between oncogenic KRAS dependency and STK33 suppression in human cancer cells); Bommi-Reddy and Kaelin Cell Research (2010) 20:119-121 (describing synthetic RAS inhibitors); Vicent et al., J. Clin. Invest. (2010) 120:3940-3952 (describing that Wilms tumor 1 (WT1) regulates KRAS-driven oncogenesis and senescence in mouse and human models); Naik et al. Hum. Cancer Biol. (2009)15:7529-7537 (describing that vascular endothelial growth factor receptor-1 is synthetic lethal to aberrant b-catenin activation in colon cancer); Zender et al. Cell (2008) 135:3911-3921 (describing an oncogenomics-based in vivo RNAi screen identifying tumor suppressors in liver cancer); Lovejoy et al. Proc. Natl. Acad. Sci. (2009) 106: 19304-19309 (describing functional genomic effector library screens to identify CINP as a genomic maintenance protein); Vasudevan et al. Cancer Cell (2009) 16:21-32 (describing AKT-independent signaling downstream of oncogenic PIK3CA mutations in human cancer); Bric et al. Cancer Cell (2009) 16:324-335 (describing functional identification of tumor-suppressor genes through an in vivo RNA interference screen in a mouse lymphoma model); Taghavi et al. Oncogene (2008) 27:6806-6816 (describing an in vitro genetic screen to identify a role for LPA signaling and c-Myc in cell transformation); Bommi-Reddy et al. Proc. Natl. Acad. Sci. (2008) 105:16484-16489 (describing a synthetic lethal screen identifying kinase requirements in human cells and alteration of the same in VHL cancer cells); Guryanova et al. Mol. Biol. (2006) 40:396-405 (describing the optimization of a genome-wide disordered lentivector-based short hairpin RNA library); Hattori et al., Blood (2007) 110:640-650 (describing an RNAi screen identifying UBE2D3 as a mediator of all-trans retinoic acid-induced cell growth arrest in human acute promyelocytic NB4 cells); and Gumireddy et al., Nature Cell Biol. (2009) 11:1297-1304 (describing the identification of KLF17 as a negative regulator of epithelial-mesenchymal transition and metastasis in breast cancer).

The disclosures and description of the types of effector libraries described in the above references are incorporated herein by reference.

The composition of effector libraries of interest may be different and may be defined by specific studies. In one type of effector library composition, the minimal effector library includes a single effector construct targeting a biological molecule (e.g., p53 protein, RAS, NFkB, myc, etc.) or a process (e.g., apoptosis, etc.) and a negative control effector construct which does not affect any molecule, function or process in the cell. Examples of negative control effector constructs are effector constructs targeting molecules which are not present in the target cells of interest, e.g., firefly luciferase, green fluorescent protein, scrambled control (RNA sequences which are not present in mammalian cells), etc. In certain embodiments, the minimal effector library includes the redundant set of the each specific effector and negative control effector construct, e.g., several unique effector molecules (with different sequences) targeting a single target molecule may be present in the library. While a given redundant set may vary, in some instances a redundant set may include 2-3, such as 5-8 and including 10 or more effectors.

Where desired, an effector construct may include a functionally validated effector sequence, e.g., validated for biological activity in a previous experiment or predicted to have a certain activity using special programs.

In some instances, the effector library employed in the genetic screen is made up of effector constructs (which are optionally functionally validated effector constructs) that target the key molecules important for cell functions. In some instances, the effector constructs target a molecule selected from the group listed at: http://cbio.mskcc.org/tcga-generanker/index.jsp, e.g.,: CDKN2A; PTEN; EGFR; TP53; PIK3CA; RB1; NF1; MET; CDK4; ATM; PDGFRA; MDM2; APC; EP300; ERCC2; KRAS; PIK3CG; BRCA1; STK11; BRCA2; ERBB2; BRAF; FBXW7; MLH1; MSH2; SMAD4; CDKN2B; FGFR3; MSH6; PIK3CB; PIK3R1; ERCC3; JAK2; KIT; RET; AKT1; PLCG1; SMARCA4; CDH1; CDKN1A; DNMT1; ERBB3; NOTCH1; CCND2; MYC; NRAS; AKT2; CREBBP; NF2; NTRK1; PDGFRB; ABL1; CCND1; CDK6; HSP90AA1; TCF3; CTNNB1; FGFR1; FIGF; HRAS; NTRK3; WT1; CDC42; EXT1; FOXO3; MDM4; PDGFA; PMS2; RUNX1; VHL; WRN; ALK; AR; CDKN2C; CHEK1; CHEK2; ERCC5; FAS; FGFR2; HDAC1; KDR; NOS3; PTCH1; TERT; TSC2; BLM; CBL; COL1A1; EVI1; MAP2K4; PDGFB; SEPT9; TGFBR2; TRRAP; EGF; FLT3; GRB2; NCAM1; NOS2; BUB1B; CDKN1B; DIRAS3; DOT1L; EPHB1; EPHB6; GNAS; HIF1A; MRE11A; PLCG2; PRKDC; PTPN11; RAD50; RAD51; SPRY2; FANCA; FANCF; FGFR4; FLT1; FOXO1; MAP2K1; PPP2R1A; PTGS2; SHC1; TPO; XPA; XPC; BAI3; BARD1; BCL2; CARM1; CDK2; CERK; DGKZ; E2F1; EPHA3; EPO; ERBB4; FANCE; FH; FLT4; IRS1; MAPK1; NBN; PLCB1; PRKCZ; SMARCB1; TCF12; TPR; VEGFA; ABCC3; CD44; CDKN2D; CSF1R; DPYD; ESR2; EWSR1; FANCD2; FOS; LMO2; NOTCH3; PARP1; PRKCA; SMAD2; SMAD3; TSC1; ADCY9; AGAP2; BAX; BCL11A; BCR; BIRC5; CAV1; CCNE1; DGKB; EPHB4; ERCC6; ESR1; ETV1; FLNC; FN1; GSK3B; HDAC2; HOXA9; MEN1; MYH9; NCOA2; PCNA; PML; PPARG; PPARGC1A; RARA; SKP2; SOCS1; SOS1; SRC; TEK; TOP2A; TPM3; ABCA1; APC2; AURKA; CCND3; CD40LG; CDX2; CEBPA; CYP19A1; DNMT3B; ERCC1; ERCC4; ETV4; FES; GAB1; HGF; IFNG; IGF2R; INSR; KLF6; MPL; MUTYH; MYCL1; NR3C1; PIK3C3; PIK3CD; PIK3R2; PPP1R3A; PPP2R1B; PTPRB; RECQL4; ROS1; RPS6KA2; SDHB; SP1; THBS1; TP73; ANAPC5; ATR; BCL3; BIRC6; BRIP1; CBFA2T3; CDC73; CDK7; CLTC; CSMD3; CSNK1 G2; CTNNA1; CYP1B1; DDB2; DGKI; ELOVL2; EP4001; EPHA8; EPHB2; ERG; EXT2; FANCC; FANCG; FRAP1; GATA1; GMPS; GPC3; HDAC4; HIPK2; HMGA1; HOXD11; IDH1; IGF1R; IGFBP3; KALRN; KAT2B; LAMA1; LAMP1; LDHA; LTBP1; MAPK3; MAPK8IP2; MINPP1; MLL; MLL3; MST1R; MUC1; MYST4; NAV3; NOTCH2; NSD1; PAFAH1B2; PAK7; PARP2; PIGS; POLE; PPP1R13L; PPP2CB; PPP2R2B; PTCH2; PTK2; PTPRD; RAD51L1; RHEB; RHOA; RPS6KA1; RPS6KB1; RUNX1T1; SDHC; SDHD; SNCG; SOCS2; SPEN; TFE3; TGFBR1; TLX1; TNK2; and ZNF331.

As reviewed above, the effector library composition of the specific effector constructs may be present separately (arrayed format) or mixed together (pooled format). In the arrayed format, a unique effector complex is transduced in the target cell, transduced cells are grown in vitro, treated if necessary (e.g., with a stimulus, such as a drug, radiation, heat shock, etc.) and the transduced cells are assayed for a specific phenotype. The benefit of arrayed format is that a variety of different biological assays developed to measure biological processes may be applied to measure cellular phenotypes and identify functional effector constructs. In the pooled format approach, the effector constructs are mixed together, e.g., at similar amounts in the final effector library, and target cells are transduced with the effector library under conditions such that the majority of the target cells are transduced with a single effector construct of the library. In some instances, the delivery of single effector construct into a given target cell is achieved under transduction conditions wherein the number of transduced cells is at least 2-fold less, such as at least 5 fold or less, than the number of distinct effector constructs of the library used for transduction. In a given genetic screen assay, the transduced cells can grow in vitro (in cell culture) or in vivo (in the model organism). The benefits of pooled formats include cost-effective protocols and the ability to apply genetic screen in ex vivo and in vivo applications. In ex vivo genetic screen applications, the pooled effector library is transduced into the target cells, transduced cells are delivered in the host organism (e.g., mouse, monkey, pig, human, etc.), the organism is treated if necessary with small molecules (e.g., drugs) and after some period of time, transduced cells are isolated that the effector composition is identified in the isolated cells. In in vivo protocols, the effector library is delivered to the target cells (e.g., by microinjection, etc.), the effector library is transduced into the target cells (e.g., cancer cells, diseased cells, etc.), the organism (or transduced cells/tissue) is treated with drugs (if necessary), and after some period of time, the transduced cells are isolated and the effector composition is identified. The functional effectors may be identified by depletion or enrichment in comparison with other effector constructs (such as negative control effector constructs) which are present in the effector library.

The particular protocol of the genetic screen used to evaluate a given effector construct or library thereof, e.g., made up of multiple effector constructs, for example multiple effector construct subsets, may vary. Specifics of a given genetic screen depend, at least in part, on the nature of the effector construct library, including the effector and vector components, the nature of the target cells that are employed, the characteristic of interest, etc. In certain embodiments, the genetic screen is employed with mammalian target cells. In certain embodiments, the target cells are human or mouse origin. Genetic screens of interest may be negative selection screens, e.g., where cell growth is evaluated by time (e.g., by measuring proliferation, death rate, etc.) or positive selection screens, e.g., where a specific phenotype e.g. for cell marker, drug resistance, migration, etc., is employed to identify, isolate or select cells and therefore identify effectors of interest.

Clonal analysis of an effector library screen in accordance with aspects of the invention is provided by employing an effector library that includes effector constructs which include an effector domain, where the effector domain includes at least an effector cassette linked to a clonal barcode, e.g., as described in greater detail below. In practicing methods of the invention, an effector construct or library thereof is contacted with a population of target cells under conditions sufficient for the effector construct(s) to enter into cellular members of the population of target cells, e.g., via transduction. In other words, the effector construct(s) and target cells are contacted with each other under transduction conditions sufficient for the target cells to be transduced with effector constructs. The effector constructs and libraries thereof employed in methods of the invention may vary greatly, where the type of effector library may be selected, at least in part, on the protocol to be employed to introduce the library members into the target cells.

Effector libraries employed in methods of the invention are made up of a plurality of effector constructs, where each effector construct includes an effector domain and a vector domain. The effector domain includes an effector cassette linked to a clonal barcode, e.g., as described in greater detail below. The vector domain may be any domain that provides for entry of the effector into a target cell. Vector domains that may be employed include, but are not limited to, vector domains that provide for entry of a single effector construct into a given target cell, where specific types of vector domains of interest include viral vector domains. Accordingly, of particular interest in certain embodiments is the use of effector libraries that employ viral vector domains. Therefore, for ease of description purposes only, further aspects of the invention will be described in terms of viral vector embodiments. However, describing these embodiments in greater detail should not be construed to mean that other types of vector domains may not be employed in methods of invention.

In those embodiments employing viral vectors in the effector libraries, members of the effector library are present as viral particles that house a viral genomic nucleic acid, where the viral genomic nucleic acid of a given particle member of the library includes both a vector domain and an effector domain (i.e., viral particle effector libraries where the effector encoding nucleic acid is encapsidated in a viral protein shell). Such libraries may be referred to as packaged viral effector libraries.

Within a viral effector library of the invention, the viral genomic nucleic acids of different library members will share common vector domains. Accordingly, the effector construct members will share a common vector sequence, such that the sequence of the encapsidated viral genomic nucleic acids in the library will be substantially, if not completely, identical, but for the effector domains of the library. The sequence of the vector domain may vary greatly, depending on the nature of the vector. In some instances, the vector domain includes sequences necessary for the production of recombinant retrovirus in a packaging cell, transduction and replication of effector construct in the target cells and expression of effector molecules, reporters or other genes. Generation of the vector domain, as well as effector libraries including the same, can be accomplished using any suitable genetic engineering techniques, including without limitation, the standard techniques of PCR, oligonucleotide synthesis, restriction endonuclease digestion, site-specific digestion, site-specific recombination, ligation, transformation, plasmid purification, and DNA sequencing.

In some instances, the vector domain is selected from a viral genome of a virus selected from the group of adenoviral, adeno-associated, vaccinia, herpes, foamy, etc. viruses, where such viruses are commonly used for gene transfer applications. In some instances, the vector domain is a retroviral vector region, such that it is a domain derived from a retrovirus. Retroviruses are any virus belonging to the family Retroviridae, comprising single-stranded RNA animal viruses characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome. In some instances, the retroviral vector region is a lentiviral vector region, e.g., a vector derived from a lentivirus. Lentiviruses are members of the retrovirus family. Lentivirus vectors may be pseudotyped with VSV-G, and have been derived from the human immunodeficiency virus (HIV), the etiologic agent of the human acquired immunodeficiency syndrome (AIDS); visan-maedi, which causes encephalitis (visna) or pneumonia in sheep; the caprine arthritis-encephalitis virus, which causes immune deficiency, arthritis, and encephalopathy in goats; equine infectious anemia virus (EIAV), which causes autoimmune hemolytic anemia and encephalopathy in horses; feline immunodeficiency virus (FIV), which causes immune deficiency in cats; bovine immune deficiency virus (BIV) which causes lymphadenopathy and lymphocytosis in cattle; and simian immunodeficiency virus (SIV), which causes immune deficiency and encephalopathy in non-human primates. Vectors that are based on HIV may retain <5% of the parental genome, and <25% of the genome may be incorporated into packaging constructs, which minimizes the possibility of the generation of revertant replication-competent HIV. The vector region may include sequences form the 5' and 3' LTRs of a lentivirus. In some instances, the vector domain includes the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Where desired, the effector library may be made up of self-inactivating vectors that contain deletions of the regulatory elements in the downstream long-terminal-repeat sequence, eliminating transcription of the packaging signal that is required for vector mobilization. As such, the vector region may include an inactivated or self-inactivating 3' LTR. The 3' LTR may be made self-inactivating by any convenient method. For example, the U3 element of the 3' LTR may contain a deletion of its enhancer sequence, such as the TATA box, Sp1 and NF-kappa B sites. As a result of the self-inactivating 3' LTR, the provirus that is integrated into the host ell genome will comprise an inactivated 5' LTR. Optionally, the U3 sequence from the lentiviral 5' LTR may be replaced with a promoter sequence in the viral construct. This may increase the titer of virus recovered from the packaging cell line. An enhancer sequence may also be included.

As summarized above, in addition to the vector domains, the genomic nucleic acids of the effector libraries employed in methods of the invention also include an effector domain. The effector domain of a given member of the effector library is a domain that at least includes a coding sequence for an effector of interest (which may be present in an effector cassette) linked to a clonal barcode. The types of effectors which may be assayed in methods of the invention may vary greatly. As reviewed above, effectors of interest include, but are not limited to: nucleic acid effectors, such as ribonucleic acid effectors, e.g., siRNA (including siRNA, shRNA, microRNA, etc.), genetic suppression elements, non-coding RNAs, long non-coding RNAs, small RNAs and ribozymes, deoxyribonucleic acid effectors, (e.g., antisense); polypeptide effectors, e.g., peptides, protein domains, proteins, etc., full-length proteins and the like. A given effector library includes a collection of distinct effector nucleic acid domains of different sequence, where the sequences of the effector library members have been selected based on the intended nature of the effector library. For example, if the effector library is a siRNA effector library, an RNA target of interest is first selected, and then various siRNA sequences are selected and distinct effector sequences are designed and synthesized. The target RNA could be mRNA, microRNA, non-coding RNA, small RNA and other types of RNAs which are expressed in the target cells and could affect cellular functions. The length of a given effector nucleic acid sequence of a given effector cassette may vary, e.g., depending on the nature of the effector library, etc. In some instances, the length of the effector sequences in the library may range from 5 to 5000 nt, such as 10 to 2000 nt, including 19 to 50 nt. In certain embodiments, the effector sequences are shRNA or microRNA in which the size of the region substantially complementary to target mRNA ranges from 19 to 30 nucleotides. The number of distinct effector sequences (and therefore cassettes) of differing sequence in a given library may vary. In some instances, the number of distinct effector sequences of differing sequence is 2 or more, e.g., 5 or more, 100 or more, 1000 or more, 5000 or more, 10000 or more, 15,000 or more, 20000 or more, 25000 or more, etc. In certain embodiments, the number of distinct effector sequences of differing sequence in a given library may range from 5000 to 50000, such as 10000 to 40000 and including 20000 to 30000. Two effector sequences are considered to be distinct if their sequences differ from each other by even a single nucleotide. In a given effector library, each effector sequence may have the same length, or different effector members of the library may have different lengths. The effector library may include a single unique effector construct or the redundant set of effectors targeting the same cellular target (e.g. mRNA).

In addition to the effector, e.g., as described above, the effector domain also includes a clonal barcode that is linked to the effector. By "clonal barcoded" is meant a barcode nucleic acid sequence. The phrases "nucleic acid barcode" and "barcode", as well as variations thereof, refer to an identifiable nucleotide sequence, such as an oligonucleotide or polynucleotide sequence. In some embodiments, nucleic acid barcodes are uniquely identifiable. In some embodiments, a nucleic acid barcode can comprise a synthetic or natural nucleic acid sequence, DNA, RNA, or other nucleic acids and/or derivatives. For example, a nucleic acid barcode can include nucleotide bases adenine, guanine, cytosine, thymine, uracil, inosine, or analogs thereof. The barcode length may vary as desired, where in some instances the length ranges from 2 to 100 nt, such as 5 to 20 nt, and in some embodiments including from 8 to 20 nt. A given barcode sequence may vary as desired. As desired, barcodes may be any sequence of 2-10 (or more) random nucleotides (e.g. A, G, C or T in every position or subset of these nucleotides). In some instances, barcodes employed are specially designed with specific unique (i.e., distinct) sequences which are significantly different from each other, even in the case of at least 1 or even 2 mutations.

Within a given library, the number of distinct clonal barcodes of different sequence represented in the effector library may vary. In some instances, the number of distinct clonal barcodes of different sequence present in the effector library is a fraction of the number of distinct effector sequences of the effector library, where the fraction may be 25% or less, such as 20% or less, including 15% or less than the number of distinct effector sequence in the library, based on number of distinct sequences. In some instances, the number of distinct clonal barcodes of differing sequence present in the library is 100 or more, such as 250 or more, e.g., 500 or more, 1000 or more, including 1500 or more, such as 2000 or more, 2500 or more, 3000 or more, 35000 or more, e.g., 5000 or more, including 10,000 or more.

Where desired, the effector cassette of the effector domain may be a "barcoded effector cassette", by which is meant that each distinct effector cassette in the effector library includes a unique identifying sequence, i.e., an effector barcode, which is distinct from the clonal barcode, e.g., as described above. Consistent with the definition provided above, the phrases "nucleic acid barcode" and "barcode" when used in conjunction with an effector barcode, as well as variations thereof, refer to an identifiable nucleotide sequence, such as an oligonucleotide or polynucleotide sequence. In some embodiments, nucleic acid barcodes are uniquely identifiable. In some embodiments, a nucleic acid barcode can comprise a synthetic or natural nucleic acid sequence, DNA, RNA, or other nucleic acids and/or derivatives. For example, a nucleic acid barcode can include nucleotide bases adenine, guanine, cytosine, thymine, uracil, inosine, or analogs thereof. The barcode length may vary as desired, where in some instances the length ranges from 5 to 100 nt, such as 10 to 30 nt, and including 12 to 20 nt. A given effector barcode sequence may vary as desired, but has at least one nucleotide difference between any effector barcode in the library. In certain embodiments, the difference between any effector barcode sequences in the set is at least two nucleotides.

Where desired, the effector domain and/or effector cassette of the domain, may further include a promoter, such that the effector sequence is under control of a suitable promoter, such as an RNA Polymerase II or III promoter, for expression of the effector molecule(s). The promoter may be operably linked to the effector sequence which also may be linked to a termination sequence, in some instances followed by effector barcode sequence, thus forming an effector cassette, e.g., for cloning and expression of the effector molecules. In addition, more than one promoter may be used to express effector molecules. An "internal" cassette is promoter/enhancer that is located between the 5' LTR and the 3' LTR sequences in the viral construct and is operably linked to the effector. In another embodiment, the effector cassette is located in the 3' LTR or, optionally, in the U3 the region of 3' LTR. In another embodiment, the internal region further may include a drug-resistance cassette (conferring resistance to Puro, Hprt, Neo, or Hyg, for example) or a reporter cassette (coding for fluorescent GFP, RFP, intracellular or cell surface marker, epitope, protein or enzymes such as luciferase or β-galactosidase, phosphatase, CD81, H2Kk, NGF receptor (extracellular domain) for example) under control of a constitutive or regulated promoter.

The promoter/enhancer for the effector, drug-resistance or reporter cassette may be selected based on the desired expression pattern of the effector and the specific properties of the promoters/enhancers. Thus, the promoter may be a constitutive promoter, such as the promoter for ubiquitin, CMV, β-actin, histone H4, EF-1 alfa or pgk controlled by RNA polymerase II, or the U6 snRNA, H1 snRNA, or tRNA promoters controlled by RNA polymerase III. Alternatively, the promoter may be a tissue-specific promoter such as Ick, myogenin, or thy1. In addition, promoters may be selected to allow for inducible expression of the effector. A number of systems for the inducible expression using such a promoter are known in the art, including the tetracycline responsive system and the lac operator-repressor system. In one embodiment, opposing promoters (attached both at the 5' end of a sense strand and at the 5' end of an antisense strand of an siRNA) is used (see WO 03/022052 A1; and US 2002/0162126 A1). An enhancer also may be present to increase expression of the effector. For example, a CMV enhancer may be used in combination with the chicken β-actin promoter.

In certain embodiments, an effector cassette comprises a Pol III promoter and an effector coding region, i.e., an effector sequence. The effector coding region of such embodiments may encode an effector molecule that down-regulates the expression level of a particular mRNA, protein or proteins. The effector molecule encoded can, for example, be a siRNA that is a double-stranded RNA complex, or an RNA molecule having a stem-loop or a so-called "hairpin" structure that inhibits gene expression of genes having an mRNA sequence complementary to one strand of the double-stranded RNA complex through a process termed RNA interference. The duplex portion of the RNA is substantially identical to a sequence of the target gene to be down regulated, and ranges in some instances from 15 to 30 nt in length. In the case of siRNA, the duplex RNA can be expressed in a cell from a single retroviral construct, such as a lentiviral construct. In one embodiment, a single RNA coding region in the construct comprises a sense region, a loop region, and an antisense region. Thus, a siRNA effector cassette may have an RNA Pol III promoter operatively linked to an RNA coding region, which includes a sense region, a loop or hairpin region, and an antisense region. The sense and antisense regions may range, in some instances, from 15 to 30 nt in length, and the loop region may range, in some instances, from 2 to 15 nt in length. Once expressed, the sense and antisense portions form a duplex with a loop at one end. The sense and antisense regions could be complementary to each other or comprise several mismatches to destabilize stem-loop structure. In another embodiment of a siRNA effector construct, the retroviral construct comprises two RNA coding regions. The first coding region is a template for the expression of a first RNA and the second coding region is for the expression of a second RNA. Following expression, the first and second RNAs form a duplex. This construct also comprises a first Pol III promoter operably linked to the first RNA coding region, and a second Pol III promoter operably linked to the second RNA region. Each coding region may be flanked on the 3' end by a terminator sequence. In yet another embodiment, the retroviral construct comprises a first RNA Pol III promoter operably linked to a first RNA coding region, and a second RNA Pol III promoter operably linked to the same first RNA coding region on the opposite strand and in the opposite direction, such that expression of the RNA coding region from the first RNA Pol III promoter results in a synthesis of a first RNA molecule as the sense strand and expression of the RNA coding region from the second RNA Pol III promoter results in synthesis of a second RNA molecule as an antisense strand that is substantially complementary to the first RNA molecule. In one such embodiment, each RNA Pol III promoter includes a termination sequence just upstream of the transcription initiation start site, such as a termination sequence having five consecutive T residues. Thus, on one strand, the Pol III promoter is linked to a first terminator sequence immediately before the transcription start site and an RNA coding region. Also in this embodiment, the expression cassette has a second Pol III promoter comprising a second terminator linked to a second coding region (substantially the complement of the first coding region). Thus, the siRNA coding sequence in such an embodiment is located, just downstream of both transcriptional start sites, without significant additional non-siRNA sequences. The RNA coding region of a siRNA effector construct may be operatively linked to a terminator sequence. The pol III terminators may include stretches of four or more thymidine residues. In some instances, a sequence of five consecutive adenines is linked immediately upstream of the RNA coding regions to serve as a terminator for the opposing promoters.

Where desired, the genomic domain may further include one or more sets of primer flanking regions, which regions may flank one or more components of the effector domain, such as the clonal barcode and effector cassette. The primer flanking regions may have any convenient length and sequence sufficient to serve as primer binding sites in amplification protocols.

The viral genomic nucleic acids of the effector libraries also may contain additional elements, where such elements may vary greatly. For example, a reporter gene may be placed in functional relationship with the internal promoter, such as the gene for a fluorescent marker protein. If a marker gene is included along with the effector, an internal ribosomal entry site (IRES) sequence can be included. Alternatively, the additional genetic elements can be operably linked with and controlled by an independent promoter/enhancer.

Since effector libraries employed in methods of invention include clonal barcodes, the effector libraries may be viewed as collections of effector sub-libraries (i.e., sub-sets), in which each effector sub-library (i.e., sub-set) includes the same effector sequence coupled to a different clonal barcoded, such that in a given effector sub-library, the effector and vector sequences are common but the clonal barcodes are distinct barcodes of differing sequence. Within an effector sub-library, the number of different clonal barcodes present in the sub-library may, in some instances, be 10 or more, such as 50 or more, including 100 or more, e.g., 500 or more, 1000 or more, 2500 or more, 3500 or more, 5000 or more, including 10000 or more. The number of different effector sub-libraries in an effector library may also vary, where in some instances the number is 2 or more, such as 5 more, such as 10 or more, e.g., 50 or more, 100 or more, 1000 or more, 5000 or more, 10000 or more, 15,000 or more, 20000 or more, 25000 or more, etc. In certain embodiments, the number of distinct effector sub-libraries in a given effector library may range from 5000 to 50000, such as 10000 to 40000 and including 20000 to 30000. As such, the complexity of an effector library, e.g., in terms of unique effector/clonal barcode combinations, may vary. In some instances, the complexity of the library is such that the effector library includes 2 or more, such as 10 or more, including 100 or more unique effector/clonal barcode combinations. In some instances, the complexity of a given effector library is chosen so as to provide a transduction step for a substantial number of distinct clones for each distinct effector in the library. In some embodiments, the substantial number may be 25 or more distinct clones, such as 50 or more distinct clones, including 100 or more distinct clones, e.g., 200 or more distinct clones, per distinct effector in the effector library.

The libraries employed in embodiments of the invention can be produced using any convenient protocol. For example, the viral and effector domains can be generated synthetically or enzymatically by a number of different protocols, and the appropriate oligonucleotide and polynucleotide constructs may be purified using standard recombinant DNA techniques as described in, for example, Sambrook et al., Molecular Cloning: A Laboratory Manual, 2nd Ed., Cold Spring Harbor Press, Cold Spring Harbor, N.Y. (1989), and under regulations described in, e.g., United States Dept. of HHS, National Institute of Health (NIH) Guidelines for Recombinant DNA Research. Where desired, the effector constructs may be synthesized synthetically using phosphoramidite chemistry. In some instances, the effector constructs are synthesized using an array-based protocol (e.g., on a surface using photolithography, ink-jet deposition, electrochemical means). See e.g., U.S. Pat. No. 7,588,889 for a description of an example of such a protocol.

In preparing the effector libraries, a library of effector constructs (i.e., pro-effector library including effector sequences, optionally linked to an effector barcode and/or in an effector expression cassette) is combined with a library of vector constructs (i.e., a pro-vector library comprising a vector domain of vector sequence) under conditions sufficient to produce product transfection plasmids which, upon transfection of a packaging cell, result in the production of viral particles containing the effector domains as part of genomic nucleic acids encapsidated in viral protein shells. Depending on the particular production protocol employed, the clonal barcode may be present in the pro-effector library or the pro-vector library, e.g., as further described below. To prepare the product transfection plasmids used for transfection, an effector domain nucleic acid is inserted into a vector nucleic acid, where any suitable protocol may be employed. Examples of suitable protocols include, but are not limited to: DNA ligase mediated joining, recombination enzyme mediate joining, using In-Fusion® PCR protocols (Clontech Laboratories, Mountain View, Calif.), etc.

Any convenient protocol may be employed to ensure that an effector domain which includes an effector cassette and a clonal barcode is operably linked to a vector domain to produce an effector construct. In a first protocol, clonal barcodes are provided in the pro-vector library, such that a plurality of distinct clonal barcodes is provided in the vector library. The number of distinct clonal barcodes represented in the pro-vector library may vary, and in some instances is 10 or more. As such, the pro-vector library is made up of nucleic acids having common vector domains but differing clonal barcodes. Since the pro-vector library includes clonal barcodes, it may be referred to as a clonally barcoded pro-vector library. This clonally barcoded pro-vector library is then employed to clone a single effector cassette or a pool of effector cassettes, e.g., the in the form of a pro-effector library. Effector libraries produced according to this protocol may be characterized in having the same number of clonal barcodes. Another synthesis protocol of interest is one in which the effector domain (which includes the clonal barcode and effector cassette) is synthesized first and then cloned into a pro-vector library that does not include clonal barcodes, i.e., a non-clonally barcoded pro-vector library. In this type of protocol, each effector domain may include on or more effector cassettes linked to one more clonal barcodes, as desired. For example, an effector domain may be described by the synthesized having a structure described by the formula effector-$N_t$ . . . , where t is an integer ranging from 2 to approximately 10 or more, and N is random nucleotide (e.g., A, G, C or T). Alternatively, both the effector and clonal barcodes have specific sequences of interest. In some embodiments, each effector may have the same or a different number of clonal bar-codes. The synthesized effector domain (which includes the clonal barcode and effector cassette, e.g., as described above) is cloned into the vector domain using any convenient protocol, thus generating the desired effector library. In some embodiments, the constituent components of the effector domains, e.g., clonal barcodes, effector sequences and, optionally effector barcodes) are synthesized separately and mixed together in a manner sufficient to produce the desired synthesized effector domains. Alternatively, the disparate components may be synthesized together as a pool, e.g., on a surface of microarray.

A specific example of one method of producing a library of effector transfection plasmids is illustrated in FIG. 1. In FIG. 1, a plurality, e.g., 27000, distinct barcoded effector domains are ligated into a plurality, e.g., 3500, distinct barcoded vector domains to produce product transfection plasmids that include a plurality, e.g., 87750, of unique effector/vector barcode combinations. As illustrated in FIG. 1, each barcoded vector includes a vector barcode sequence (which serves as the clonal barcode in the library) and a vector sequence, where the vector sequence include viral vector sequences, e.g., as described above. Each barcoded effector domain includes an effector, illustrated as a shRNA coding sequence and an effector barcode. Upon ligation of the effector domains into the vector domains, the production transfection plasmids include juxtaposed effector/vector barcodes.

The resultant product transfection plasmids may then be used to transfect a suitable packaging cell line for production of effector library viral particles. The packaging cell line provides the viral proteins that are required in trans for the packaging of the viral genomic RNA into viral particles. The packaging cell line may be any cell line that is capable of expressing retroviral proteins, including 293, HeLa, D17, MDCK, BHK, and Cf2Th. In some embodiments, the effector construct is used together with a viral reporter construct which may comprise one or more reporter genes under the control of a constitutive or conditional (regulatable) promoter. In one embodiment, at least one of the reporter genes is controlled by a signaling pathway-specific promoter (conditional) and a second reporter gene is controlled by a constitutive promoter. The packaging cell line may stably express necessary viral proteins. Such a packaging cell line is described, for example, in U.S. Pat. No. 6,218,181. Alternatively, a packaging cell line may be transiently transfected with plasmids comprising nucleic acids that encode the necessary viral proteins. In another embodiment, a packaging cell line that does not stably express the necessary viral proteins is co-transfected with two or more plasmids. One of the plasmids comprises the viral construct comprising the effector. The other plasmid(s) comprises nucleic acids encoding the proteins necessary to allow the cells to produce functional virus that is able to infect the desired host cell. The packaging cell line may not express envelope gene products. In this case, the packaging cell line will package the viral genome into particles that lack an envelope protein. As the envelope protein is responsible, in part, for the host range of the viral particles, the viruses preferably are pseudotyped. A "pseudotyped" retrovirus is a retroviral particle having an envelope protein that is from a virus other than the virus from which the RNA genome is derived. The envelope protein may be from a different retrovirus or a non-retrovirus. One envelope protein is the vesicular stomatitus virus G (VSV-G) protein. Thus, the packaging cell line may be transfected with a plasmid comprising sequences encoding a membrane-associated protein, such as VSV-G, that will permit entry of the virus into a host cell. One with skill in the art can choose an appropriate pseudo type for the host cell used. In addition to conferring a specific host range, a chosen pseudo type may permit the virus to be concentrated to a very high titer. Viruses alternatively can be pseudotyped with ecotropic envelope proteins that limit infection to a specific species.

In practicing methods of the invention, the genetic screen is performed according to any convenient protocol. Generally, the effector library is contacted with a population of target cells in a manner sufficient for members of the effector library to be taken up by the target cells. For example, where the effector library is a viral particle effector library, the library may be contacted with the population of target cells under suitable transduction conditions. Transduction of the target cells with the pre-packaged viral effector library may be accomplished by any convenient protocol and may depend, at least in part, on the target cell type and the viral vectors employed. The transduction conditions may be optimized in order to achieve delivery and expression of single unique effector-clonal bar code construct into a given target cell. The target cells can be a pure, homogeneous population of the same or similar cells or the target cells can be a heterogeneous population of different cell types. The target cells may be cultured, or may be tissues, organs, biological fluids or whole organisms, where the organism is (in some instances) a human, mouse or rat. The effector library may be co-transduced with a reporter vector in order to extend selection of target cells to a variety of in vivo and in vitro biological assays.

Figure 2:
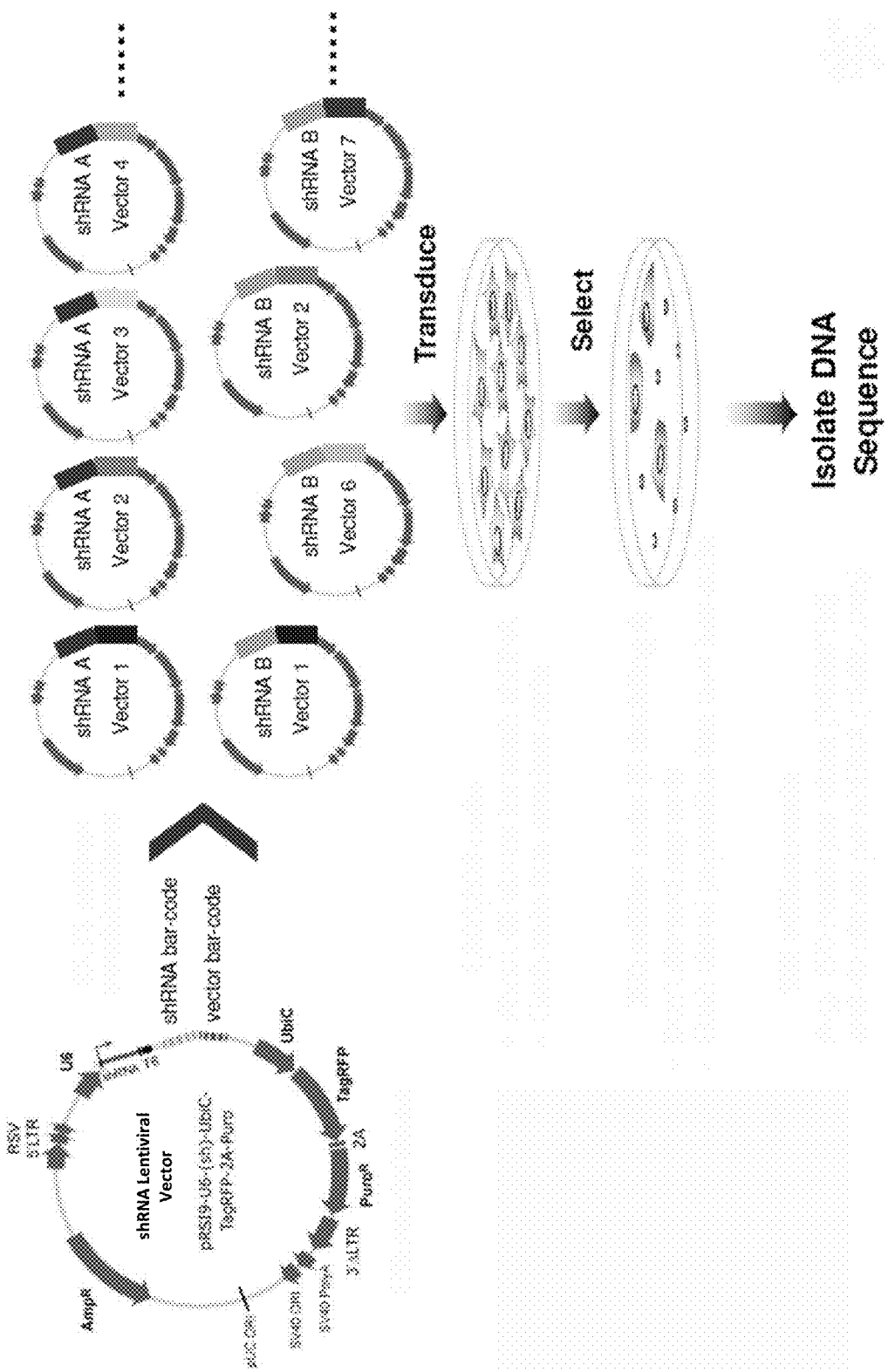
FIG. 2 illustrates a genetic screening protocol using the effector library prepared as illustrated in FIG. 1.

The number of target cells that are contacted and transduced with the effector library may be selected so as to provide for sufficient clonal analysis, such that the number may be chosen in view of the complexity of the effector library. As such, the number of target cells that is transduced with the effector library may be optimized so that the number of transduced cells is more than number of effector constructs in the effector library. Under these conditions each effector construct will be transduced in a redundant number of target cells. In some instance, the number of target cells transduced with the each effector construct in the effector library and each comprising unique clonal barcode is 10-fold or greater, such as 100-fold or greater, including 200-fold or greater. In order to achieve, the redundant set of transduced cells for the each effector construct, the number of transduced cells is optimized in order to be 10-fold or more, such as 100-fold or more, than the total complexity of the effector library, including complexity of effectors and clonal barcodes. An example of a transduction step is illustrated in FIG. 2. In this example, the library includes more than a million (e.g., 87.75 million) unique effector constructs, which may be used to transduce, e.g., 1 million cells. The transduction may generate, e.g., about 40 clones for each shRNA, where each clone has its own barcode. The transduced cells may be expanded (e.g., for 8 doubling resulting in 250 million cells) to generate clonal populations, where each clonal population has its own barcode. Nucleic acids may be isolated and sequenced, e.g., to produce 100 million reads (100 reads per clone on average (100M/1M); 40 clones per shRNA (1M/27,000)).

Once transduced, the target cells can be assayed for a particular characteristic (e.g., phenotype) of interest. Assay protocols may be pooled or array formats, as desired. Selection strategies of such assays may vary, as desired, where the particular selection strategy employed depends, at least in part, on the characteristic of interest. As summarized above, the characteristic of interest may vary greatly, ranging from growth rate to the appearance of a particular phenotype of interest, such as the expression of a reporter construct, specific marker, etc. Where desired, high throughput protocols may be employed. Where desired, the assay may include a step of exposing the cells to a stimulus, e.g., exposure to an active agent, drug, a physical stimulus (e.g., mechanical strain), and electromagnetic radiation stimulus, etc. The transduced cells could be analyzed for specific phenotype or isolated (selected) based on specific phenotype.

In the embodiment of using pooled format effector library, following selection of cells having the characteristic of interest, the cells may be further analyzed to identify both the clonal barcode and the particular effector present in the cell and at least putatively giving rise to the characteristic of interest. The clonal barcode and effector may be identified using any convenient protocol. Protocols of interest include, but are not limited to: sequencing protocols, e.g., high throughput sequencing protocols, and hybridization protocols, e.g., array based hybridization protocols. A given protocol may include various steps well-known to those of skill in the art, including but not limited to: nucleic acid amplification, e.g., to produce amplicons of the effector domains, separation, hybridization, labeling, label detection, sequencing, etc. Whatever protocol is employed, the protocol is adapted to identify not only the effector but also the clonal barcode. For example, where sequencing protocols are employed, the sequencing protocol will determine the sequence of not only the effector and/or its barcode (if present) but also the clonal barcode. Where hybridization protocols are employed, probes that bind to targets having both the effector domain of interest (e.g., effector sequence and/or barcode) as well clonal barcode may be employed. For example, where the members of the library include clonal and effector barcodes positioned in tandem, the arrays will include probes for each of the possible clonal effector tandem combinations in the initial library. In that way, the clonal barcodes are readily identified.

In some instances, the genetic screen is one that includes a high throughput selection and clonal barcode/effector identification protocol, which may be viewed as a high-throughput screening (HTS) protocol, e.g., where the effector libraries are screened in a pooled format. In certain embodiments, these embodiments exploit the advantages of high-throughput (HT) sequencing platforms to rapidly identify enriched effector inserts, inter alia, in FACS-selected cell fractions wherein particular members of the library are identified by activation of a detectable reporter gene. The identities of the effectors in the sorted population are then ascertained by rescue of the effector inserts from the vectors integrated into the cellular genomes by, inter alia, polymerase chain reaction (PCR) amplification and cloning thereof. To this end, the constructs of the invention may include primer binding sites flanking the effector domain, e.g., as described above.

Once the clonal barcode and effector are identified, the resultant data may be employed in clonal analysis of the genetic screen, e.g., as described above. Because each different transducing effector construct is clonally barcoded and the barcode is identified, the number of different clonal populations (and therefore individual precursor target cells actually transduced with a member of the effector library) may be readily determined. This information may then be used for a variety of different purposes.

The methods of clonal analysis, e.g., as described herein, may be employed in a variety of different genetic screens for a variety of different purposes. Examples of applications in which clonal analysis may be employed include, but are not limited to: determination of effector toxicity, identification of effectors which block or enhance action of drugs, modulate effect of physical treatment, signaling pathways, biological process in the target cells, etc.

In some instances, methods as described herein may be employed to determine the inherent toxicity of a given effector in an effector library. For example, as reviewed above, a given effector library may include a number of different effector sub-libraries, where each sub-library includes members having a common effector sequence but distinct clonal barcodes. By assuring that the complexity of the effector library is sufficient relative to the number of target cells initially transduced, the methods can be practiced such that the number of original transduced cells at infection is kept at 10-100 cells/for each different effector, such as shRNA, in the library. In such embodiments, the 10-100 clones (i.e., cell populations arising from an individual transduced cell) for each effector are independent replicates of the biological experiment and can therefore be used for independent measurements of the toxic effect of each effector, e.g., shRNA. Different data analysis strategies can be applied to clonal effector enumeration data. One embodiment of identifying toxic effectors employs clonal analysis to identify statistically significantly depleted effectors from a single transduction of a pooled effector library. In the course of a medium-term, 8-10 cell population doubling experiment, the clonal size sample of a non-toxic effector is expected to be randomly and symmetrically distributed around the value of the clone's size of the uninfected cells. For toxic effectors, it is expected that the majority of the originally transduced cells will produce clones of smaller size or may completely disappear. A small but significant number of clones are expected to be in the size range typical to non-toxic effector clones, because it is common for a small fraction of starting cells not to express enough effector levels from the integrated construct or to express mutated inactive effector sequences. So for toxic effectors, an asymmetrical right-skewed distribution of the clonal sizes is expected, as well as a less than expected number of clones compared to nontoxic effectors of similar initial concentration in the effector library. The latter can be reformulated so that for toxic and non-toxic effectors with similar final (end of experiment) representation in the library, the toxic effectors will have a bigger number of clones. This method of post-hoc pair selection enables the use of multiple negative control effectors in the library as reference points instead of the distribution of the effector constructs in the plasmid library. This approach provides for the use of large size libraries since it allows screens to be performed with a smaller number of transduced cells, with tolerance to possible deformation of the original representation of the effector in the plasmid library.

Figure 3:
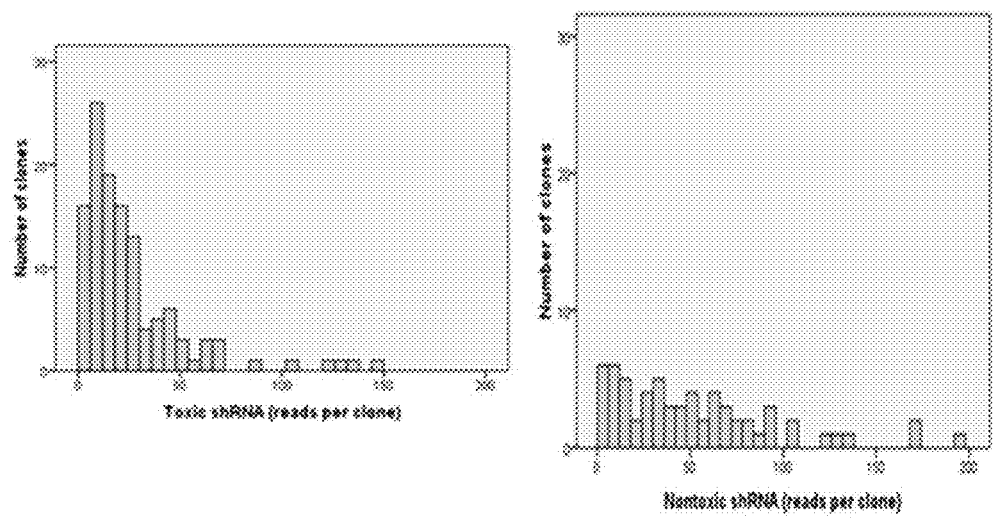
FIG. 3 provides an example of clonal analysis of effector toxicity obtained in viability screen with the complex effector library, comprising clonal barcodes, according to an embodiment of the invention.

The example shown in FIG. 3 shows how the observed distribution of the sizes and numbers of clones for one toxic effector and one non-toxic control effector in a typical double barcoded effector library screen perfectly match the theoretically expected distributions. Comparison of the two distributions can be performed using standard two-sample approaches with non-parametric methods that are sensitive not only to difference in group central tendency but to difference in the shape of the distributions (e.g., Kolmogorov-Smirnov test). Thus, this new approach enables one to implement statistical methods for samples of 50-100 independent repeats (clones) within a single viral transduction, which is a much larger number than would be typically possible in standard single barcode effector screens. For more sophisticated investigations of biological processes, other approaches can be used for clonal effector data analysis, but applying the popular robust nonparametric tests is sufficient for the purpose of identifying toxic effectors from negative selection screens.

The following examples are offered by way of illustration and not by way of limitation.

EXPERIMENTAL

I. Construction of Clonal Lentiviral shRNA Library

Development of clonal shRNA library is based on construction of a collection of lentiviral vectors comprising distinct clonal barcode cassettes (Step 1), followed by cloning of shRNA cassette (with shRNA-specific barcode) into the developed clonal barcode lentiviral vectors (Step 2). While the following description is described in terms of Step 1 followed by Step 2, in alternative embodiments Steps 1 and 2 can be combined together by cloning dual shRNA-clonal barcode cassette or the shRNA cassette could be cloned first, followed by cloning of clonal barcode cassette.

Step 1. Cloning of Clonal Barcode Cassette in pRSI Lentiviral Vector.

Clonal barcode cassettes (see FIG. 4) having 3,250 unique 14-nucleotide long barcodes (differing from each other by at least 2 nucleotides) flanked by known flanking sequences were synthesized on the surface of custom microarray and provided as oligonucleotide pool (Agilent, Santa Clara, Calif.). The oligonucleotide pool (0.2 pmol) was amplified on a PE 9700 (Life Technologies) in a 100-µl reaction which contained 1×Phusion GC buffer, 0.2 mM dNTP, 0.5 µM of the each flanking FwdBC1 and RevBC1 primers (FIG. 5) and 1 unit of Hot Start Fusion DNA polymerase (Finnzymes). Cycling parameters were 98° C. for 30 s, 2 cycles of 98° C. for 10 s, 55° C. for 2 min, 72° C. for 20 s, followed by 12 cycles of 98° C. for 10 s, 65° C. for 10 s, 72° C. for 20 s. The amplified pooled clonal barcode cassettes (approximately 2 µg of DNA) were purified using PCR purification kit (Qiagen) according to the manufacturer's recommendations and digested in 100-µl reaction containing 1×G+ buffer and 100 u of BpiI restriction enzyme (Fermentas) in air incubator at 37° C. for 2 hours. The Bpi-digested clonal barcode cassettes were then separated by electrophoresis in 3.5% agarose-1×TAE gel, cut out and extract from the gel using QIAquick gel purification kit (Qiagen).

To prepare the vector for cloning, 5 µg of pRSI9-U6-UbiC-RF-2A-Puro (FIG. 4) was subjected to restriction digest in a 100-µl reaction containing 1×G+ buffer and 100 u of BpiI restriction enzyme (Fermentas) in air incubator at 37° C. for 2 hours. The Bpi-digested lentiviral vector was then separated by electrophoresis in 1.2% agarose-1×TAE gel followed by purification using QIAquick gel purification kit (Qiagen).

A Clonal 3.2K lentiviral shRNA library was prepared by ligation of 200 ng of BpiI-digested vector and 100 ng of clonal barcode cassette in 50-µl reaction containing 1×Ligase buffer and 200 u of T4 DNA ligase (NEB) with incubation at 16° C. for 6 hours. The ligated clonal 3.2K library was then precipitated by centrifugation by adding 2.5 volume of ethanol, following by washing with 80% ethanol. The resultant product was then dissolved in 5-μl of water and electroporated in 50-μl of SURE cells (Stratagene) in 1 mm cassette using single 1.8 kV pulse and Gene Pulser electroporator (BioRad). Electroporated SURE cells were grown in 500-ml of LB media with 100 μg per ml ampiciline at 37° C. overnight and collected cell pellet was used to purify approximately 200 μg of plasmid clonal 3.2K library with Endo-free Midi plasmid purification kit (Qiagen) according to manufacturer's protocol.

An example construction and design of a clonal barcode library is shown in FIG. 5. In this example, a 3.2 clonal barcode library in pRSI9-U6 wt-BC14-UbiC-tagRFP-2A-Puro was constructed and designed. 3.2K clonal barcode library (FIG. 5C (design of 3.2K BC14 library)) was constructed by the cloning of 3,250 14-n unique bar-codes synthesized on the surface of Agilent's microarray (FIG. 5A (design of clonal barcode cassette)), amplified using FwdBC1 and RevBC1 primers, digested with BsmBI and cloned in Bpi-digested pRSI9 vector (FIG. 5B (design of cloning site in pRSI9 vector downstream of U6 promoter)). The 3.2K BC14 vector/library could be used for cloning individual or library of shRNA constructs in BpiI/BpiI cloning sites (<u>ACCG</u> and <u>TTCG</u>). In order to use clonal barcode library as is (e.g. for barcoding cells), BC14 barcodes need to be amplified from genomic DNA using two rounds of PCR using combination of Fwd-U6-1/Rev-cPPT5 primers in the first round of PCR followed up by second round of nested PCR with combination of Gex1 MS-U6-2 and Gex2M primers. The amplified BC14 PCR products comprise primers (Gex1 MS and Gex2M) compatible with single read (SR) flow cell (Illumina's GAIIX or HiSeq2000 machine) and could be sequenced with GexSeqM sequencing primer.

Step 2. Construction of Clonal shRNA Effector Library.

Figure 4:
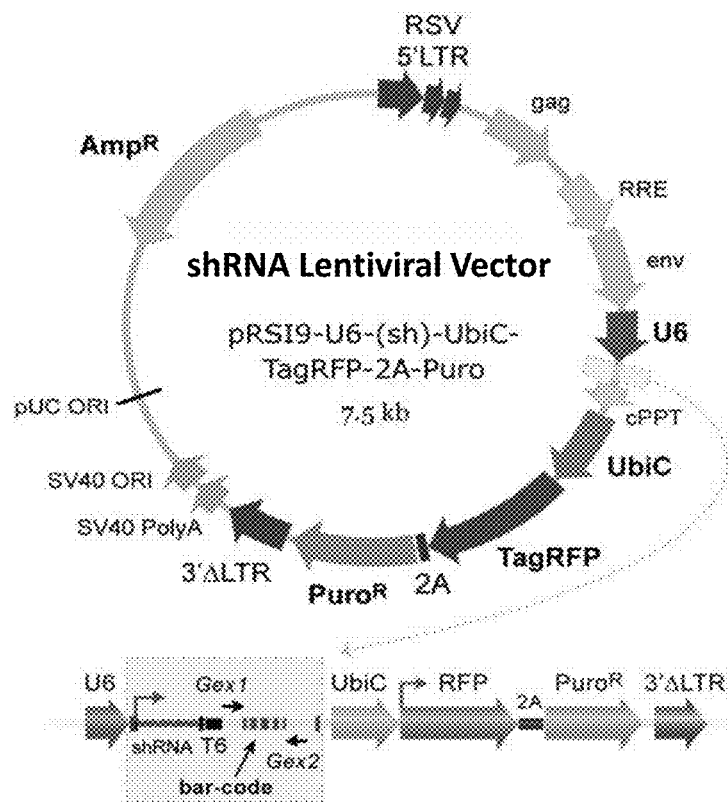
FIG. 4 provides a vector map of shRNA Lentiviral vector employed in the Experimental section, below.

The step produces a 27K shRNA library targeting 5,000 human genes by cloning 27K shRNA-barcode cassettes into a 3.2K clonal barcode library described above. Using the RNAi consortium database freely available through Broad Institute website having an address made by placing "http:// www" before "broadinstitute.or/rnai/trc/lib" , a redundant set of 5 shRNAs for the each of the 5,000 target genes was selected. The list of shRNAs and target genes is available at the website having an address made by placing "www." before "decipherproject.org". The output shRNA sequences were then modified to design a 132-nucleotide shRNA cassette for each sequence that had an extended 21 to 25 nucleotide long stem, 7-nucleotide loop (ATAACAA), and 1-2 GU mismatches in the sense portion of shRNA for equal representation of shRNA constructs in the library and for the highest knockdown efficacy in pooled format screen. The resultant shRNA cassettes also incorporated unique 18-nucleotide bar-codes (for the each specific shRNA) with upstream FwdHTS and Gex2 primer binding sites for easy identification of shRNA constructs through HT sequencing and flanked with common primer binding sites for amplification and cloning of BpiI-digested pooled shRNA cassette into the lentiviral vector clonal 3.2K lentiviral library (see Step 1 above), which drives constitutive expression of 25-nucleotide short hairpin shRNAs from human U6 promoter, tagRFP reporter and puromucin-resistance marker proteins separated by self-cleavable 2A peptide from human ubiquitin C promoter (FIG. 4). The shRNA cassettes were synthesized on a surface of a custom microarray by Agilent Technologies (Santa Clara, Calif.) and provided as an oligonucleotide pool (10 pmol) with complexities of 27,000 of shRNA-barcode oligos.

The oligonucleotide pool (0.2 pmol) was amplified on a PE 9700 (Life Technologies) in a 100-μl reaction, containing 1×Phusion GC buffer, 0.2 mM dNTP, 0.5 μM of the each flanking FwdPool10 and RevPool10 primers (FIG. 6) and 1 unit of Hot Start Fusion DNA polymerase (Finnzymes). Cycling parameters were 98° C. for 30 s, 2 cycles of 98° C. for 10 s, 55° C. for 2 min, 72° C. for 20 s, followed by 12 cycles of 98° C. for 10 s, 65° C. for 10 s, 72° C. for 20 s. The amplified pooled shRNA-barcode cassettes (approximately 2 μg of DNA) were purified using PCR purification kit (Qiagen) according to manufacturer's recommendations and digested in 100-μl reaction containing 1×G+ buffer and 100 u of BpiI restriction enzyme (Fermentas) in air incubator at 37° C. for 2 hours. The Bpi-digested shRNA cassettes were then separated by electrophoresis in 3.5% agarose-1× TAE gel, cut out and extract from the gel using QIAquick gel purification kit (Qiagen).

To prepare the clonal 3.2K vector/library for cloning, clonal 3.2K library generated at step 1 (5 μg) was subjected to restriction digest in a 100-μl reaction containing 1×G+ buffer and 100 u of BpiI restriction enzyme (Fermentas) in air incubator at 37° C. for 2 hours. The Bpi-digested lentiviral 3.2K library was then separated by electrophoresis in 1.2% agarose-1×TAE gel followed by purification using QIAquick gel purification kit (Qiagen).

Pooled lentiviral clonal 27K shRNA shRNA library was prepared by ligation of 200 ng of BpiI-digested clonal 3.2K library and 100 ng of shRNA-barcode cassette in 50-μl reaction containing 1×Ligase buffer and 200 u of T4 DNA ligase (NEB), and were incubated at 16° C. for 6 hours. The ligated clonal shRNA library was precipitated by centrifugation after adding 2.5 volume of ethanol, washed with 80% ethanol, dissolved in 5-μl of water and electroporated in 50-μl of SURE cells (Stratagene) in 1 mm cassette using single 1.8 kV pulse and Gene Pulser electroporator (BioRad). Electroporated SURE cells were grown in 500-ml of LB media with 100 μg per ml ampiciline at 37° C. overnight and collected cell pellet was used to purify approximately 200 μg of plasmid clonal 27K shRNA library with Endo-free Midi plasmid purification kit (Qiagen) according to the manufacturer's protocol.

Figures 6A, 6B, 6C:
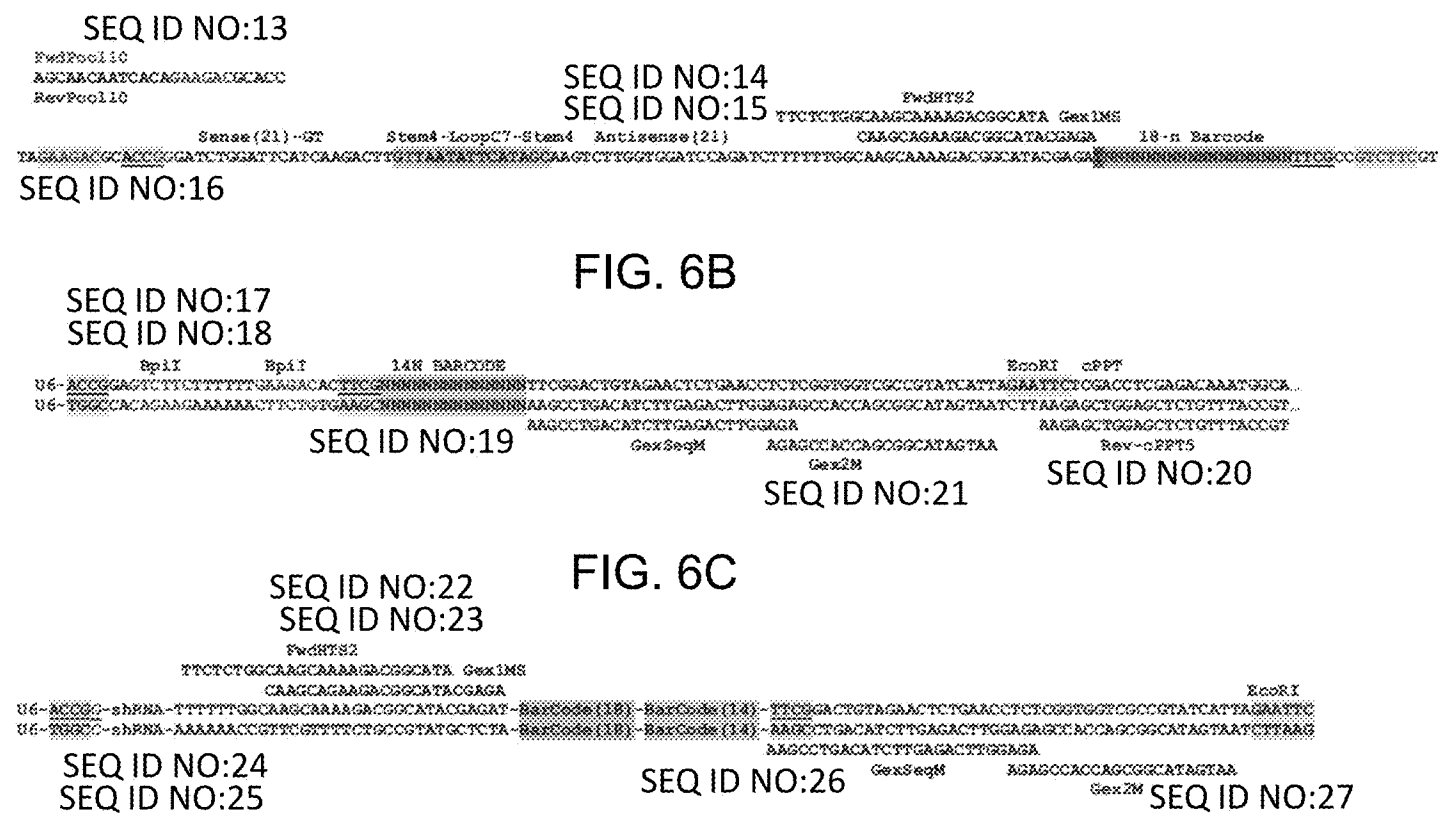

The design of a clonal 27K shRNA library is shown in FIG. 6. 27K barcoded shRNA cassette (FIG. 6A) was synthesized on the surface of Agilent's microarray, amplified with flanking FwdPool10 and RevPool10 primers and after digestion with BpiI cloned in Bpi-digested 3.2K clonal barcode library (FIG. 6, panel B). The developed clonal 27K shRNA library includes an shRNA portion (FIG. 6 A) 18-n shRNA specific barcode and each shRNA construct has approximately 3.2K 14-n clonal barcodes. For representation analysis 18-n shRNA-specific and 14-n clonal barcodes can be amplified from genomic DNA of transduced cells in the first round of PCR with FwdHTS2 and RevcPPT5 primers, followed by second round of nested PCR with Gex1 MS and Gex2M primers and sequenced using GexSeqM primer.

As shown in FIG. 6A, the barcoded shRNA cassette includes shRNA portion (with 25 bp stem portion 7n loop and TTTTTT terminator), primer-binding portion, 18-n shRNA-specific barcode and flanked on both sides with primer-binding site sequences comprising Bpi sites (GAAGAC) necessary for amplification and cloning (after BpiI digestion) in the AACG and TTCG sites in the clonal barcode library. Details regarding the construction of the clonal barcode library shown in FIG. 6B are provided in FIG. 2. As shown in FIG. 6C, the clonal shRNA library comprises U6 promoter, which drive expression by RNA polymerase III of downstream shRNA, terminator (TTTTTT) for RNA polymerase III, primer-binding region, 18-n shRNA-specific barcode, 14-n clonal barcode and primer-binding region. For representation analysis of both shRNA-specific and clonal barcodes, the dual BarCode(18)-Barcode(14) region is amplified by FwdHTS2 and RevcPPT5 primers in the first round of PCR, followed by second round of nested PCR with Gex1 MS and Gex2M primers. The dual barcode cassette is sequenced in Illumina platform using GexSeqM sequencing primer.

II. Amplification and HT Sequencing of shRNA-Specific and Clonal Barcodes from Genomic DNA of Samples after Genetic Screen The approximately $5-10 \times 10^7$ cells after the genetic screen were collected by centrifugation and the cell pellet was lysed by adding 1 ml of 0.1 MTrisHCl, 1% SDS buffer. Genomic DNA was fragmented by passing it 5 times through 22-gauge syringe, purified by two rounds of phenol/chloroform extraction, precipitated by adding 2.5 volumes of ethanol, washed with 80% ethanol and dissolved in TE buffer. The pooled bar-codes were amplified from genomic DNA by two rounds of PCR. In the first round of PCR, the $2 \times 100$-μl reaction contained 200 μg of genomic DNA (from the each sample), 1× Titanium buffer, 0.2 mM dNTP, 0.3 μM FwdHTS2 primer, 0.3 uM Rev-cPPT5 primer, 2 u of Titanium Taq DNA polymerase (Takara). The reaction mixture was subjected by 18 cycles of PCR using the following program: 94° C. for 30 s, 65° C. for 10 s, 72° C. for 20 s. Then 8 PCR reactions were combined together and 1-μl aliquot from the first PCR was amplified in the second round of PCR with nested primers in the 100-μl reaction containing 1× Titanium buffer, 0.2 mM dNTP, 0.5 μM Gex1 MS primer, 0.5 μM Gex2M primer, 2 u of Titanium Taq DNA polymerase (Clontech) which was subjected to 12 cycles PCR using the following program: 94° C. for 30 s, 65° C. for 10 s, 72° C. for 10 s. The resultant amplified pooled cassettes comprising both shRNA-specific and clonal barcodes (see FIG. 3) were then separated by electrophoresis in 3.5% agarose-1×TAE gel, cut out, extracted from the gel using QIAquick gel purification kit (Qiagen) and adjusted to 10 pM concentration. The HT sequencing of the pooled amplified bar-codes was performed using an Illumina Genome Analyzer 2000 using GexSeqM primer with approximately $100 \times 10^6$ reads (per sample) according to the manufacturer's protocol.

III. Negative Selection Screens

Viral packaging transduction and titering were performed as described in Decipher Manual (Cellecta Inc; see the website having an address made by placing "www." before "cellecta.com/resources/literature". A dual barcoded 27,000-shRNA viral library targeting 5,000 genes (5shR-NAs/gene) (prepared as described above) was used. Three independent transductions were performed. Each transduction consisted of 10,000,000 cells infected at 50% efficiency so that about 5,000,000 cells were transduced (about 200 cells/shRNA on average). All the different clones derived from the independently transduced cells and expressing the same shRNA will carry the same shRNA-specific primary barcode, but each independent clone will also carry a different clonal secondary barcode. Note: depending on the number of shRNAs in the library, the number of available secondary (clonal) barcodes, and the number of reads/sample available in High throughput sequencing, the operator could set the average number of originally transduced cells/shRNA to any value equal or greater than 10 (assuming that 10 clones/shRNA is the minimum number of clones for statistical analysis of clone size distribution). In these particular experiments the value 200 clones/shRNA is chosen based on (i) available 10,000 secondary (clonal) barcodes (50-fold excess of secondary barcodes over transduced cells for each average shRNA), (ii) 200 million reads/sample in HT sequencing: 200 clones/shRNA for 25,000 shRNAs means 500,000 total clones, which gives on average 40 available reads/clone, which is enough reads for accurate clone size measurement.

A. Identification of Genes Essential for Viability of DU145 Human Prostate Cancer Cells: Clonal Analysis of Negative Selection Drop-Out Screens, In Vitro and In Vivo.

1. In Vitro Experiment

Day 1.

DU145 human prostate cancer cells were trypsinized and resuspended to a density of 200,000 cells/ml in D-MEM supplemented with 10% FBS and 5 μg/ml Polybrene. 25 ml of cells were aliquoted to each of six 15-cm plates (two plates for each independent experimental replicate of 10,000,000 cells), and enough virus was added to achieve 2,500,000 infected cells per plate (5,000,000 infected cells/experimental replicate). Cells were returned to $CO_2$ incubator and grown under standard conditions overnight.

Day 2.

At 18 hours post-transduction, media containing virus/Polybrene was replaced with fresh media (without Polybrene).

Day 4.

At 72 hours post-transduction, puromycin was added to the samples at a final concentration of 1 μg/ml (about 90% RFP+ cells were expected to be also puromycin resistant, based on RFP/Puro® titer assay). Puromycin selection was carried out for 48 h.

Day 9.

Samples were harvested and Genomic DNA was extracted and purified (see Decipher Manual). shRNA insert bar-codes were amplified from genomic DNA and enumerated by HT sequencing.

2. In Vivo Experiment

Day 1.

DU145 human prostate cancer cells were trypsinized and resuspended to a density of 200,000 cells/ml in D-MEM supplemented with 10% FBS and 5 μg/ml Polybrene. 25 ml of cells were aliquoted to each of twelve 15-cm plates (four plates for each independent experimental replicate of 20,000,000 cells), and enough virus was added to achieve 2,500,000 infected cells per plate (10,000,000 infected cells/experimental replicate). Cells were returned to $CO_2$ incubator and grown under standard conditions overnight.

Day 2.

At 16 hours post-transduction, cells were trypsinized and injected subcutaneously in immune-deficient mice (four injections/replicate, about 6,000,000 cells/injection)

Week 3.

3 weeks after injection, developed tumors were harvested, finely minced, and Genomic DNA was extracted and purified from treated and untreated samples (see Decipher Manual). Dual bar-codes were amplified from genomic DNA and enumerated by HT sequencing.

Figure 7:
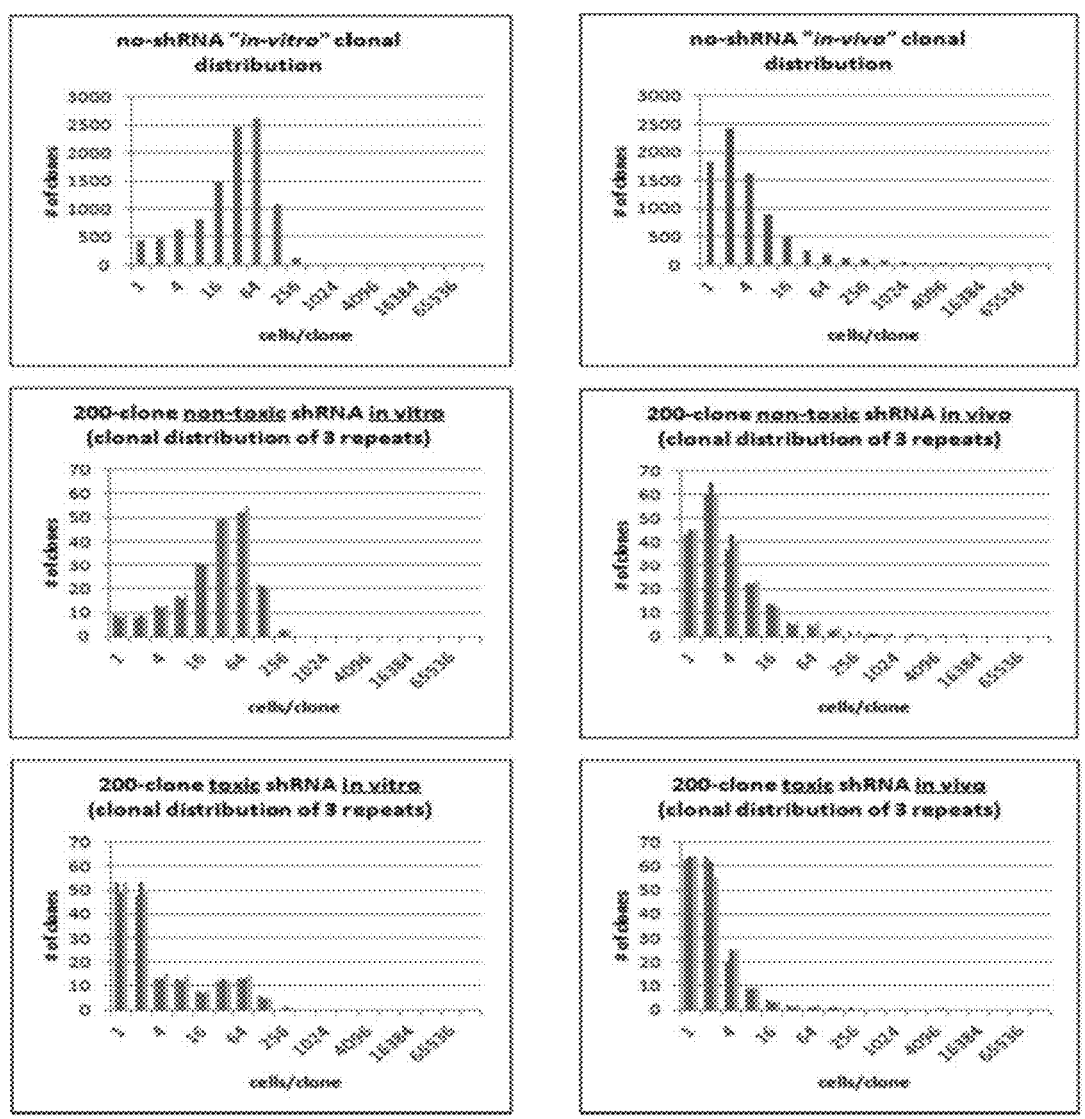
FIG. 7 provides graphical results of negative selection screens reported in the Experimental section below.

3. Data Analysis of Negative Selection Screens:

The clonal analysis approach was used for the identification of toxic shRNAs which were statistically significantly depleted from independent transductions of a pooled shRNA double-barcoded library. After several cell population doublings, either in a tissue culture experiment (in vitro) or in a xenograft tumor growth experiment (in vivo), the size of all the clones expressing a same non-toxic shRNA will randomly quasi-symmetrically distribute around the value of the average clone's size of non-shRNA expressing cells. For toxic shRNAs, a higher percentage of the originally transduced cells will produce clones of smaller size or will not produce clones at all. So for toxic shRNAs, a skewed distribution of the clonal sizes is expected, with an increased number of small-size clones as well as a less than expected number of total clones compared to nontoxic shRNAs of similar initial concentration in the plasmid library. FIG. 7 shows an example of the distribution of the sizes and of clones for one toxic shRNA and one non-toxic control shRNA in a typical double barcoded shRNA library screen, in vitro (tissue culture) and in vivo (tumor formation). Comparison of the two distributions can be performed using standard two-sample approaches with non-parametric methods that are sensitive not only to differences in group central tendency but also to differences in the shape of the distributions (e.g., Kolmogorov-Smirnov test). Thus, this new approach enabled the implementation of statistical methods for samples of 50 or more independent repeats (clones) within a single viral transduction, which is a much larger number than would be typically possible in standard single barcode RNAi screens. For more sophisticated investigations of biological processes, other approaches can be used for clonal shRNA data analysis for samples of 10 or more independent clones.

IV. Positive Selection Screens

Viral packaging transduction and titering were performed as described in Decipher Manual (Cellecta Inc; see the website having an address made by placing "www." before "cellecta.com/resources/literature". A dual barcoded 27,000-shRNA viral library targeting 5,000 genes (5shRNAs/gene) (prepared as described above) was used. 6 independent transductions were performed. Each transduction consisted of 10,000,000 cells infected at 50% efficiency so that about 5,000,000 cells were transduced (about 200 cells/shRNA on average). All the different clones derived from the independently transduced cells and expressing the same shRNA will carry the same shRNA-specific primary barcode, but each independent clone will also carry a different clonal secondary barcode. Depending on the number of shRNAs in the library, the number of available secondary (clonal) barcodes, and the number of reads/sample available in High throughput sequencing, the operator could set the average number of originally transduced cells/shRNA to any value equal or greater than 10 (assuming that 10 clones/shRNA is the minimum number of clones for statistical analysis of clone size distribution). In these particular experiments the value 200 clones/shRNA is chosen based on (i) available 10,000 secondary (clonal) barcodes (50-fold excess of secondary barcodes over transduced cells for each average shRNA), (ii) 200 million reads/sample in HT sequencing: 200 clones/shRNA for 25,000 shRNAs means 500,000 total clones, which gives on average 40 available reads/clone, which is enough reads for accurate clone size measurement.

A. Identification of shRNAs Conferring Resistance to TGF-β Mediated Apoptosis in Hep3B Human Hepatocellular Carcinoma Cells, In Vitro.

Day 1.

Cells were trypsinized and resuspended to a density of $1\times10^5$ cells/ml in D-MEM supplemented with 10% FBS and 5 µg/ml Polybrene. 25 ml of cells were aliquoted to each 15-cm plate (6 plates per replicate, $1.5\times10^7$ cells per replicate), and enough virus was added to achieve ~$9\times10^5$ infected cells per plate. Cells were returned to $CO_2$ incubator and grown under standard conditions for 24 hours.

Day 2.

18 h hours post-transduction, media containing virus/Polybrene was replaced with fresh media (without Polybrene).

Day 5.

96 h hours post-transduction, three (3) samples were harvested and stored as frozen cell pellets (untreated samples). Three cell samples were treated with DMEM media supplemented with TGF-β (1 ng/ml) to induce apoptosis.

Day 8.

After three days of TGF-β treatment, cells that survived apoptosis were trypsinized, harvested, and centrifuged, and each sample was stored as a frozen cell pellet (TGF-β treated samples).

Genomic DNA was then extracted and purified from the all 6 cell populations (both TGF-β treated and untreated samples). Dual bar-codes were amplified from the entire amount of isolated genomic DNA and enumerated by HT sequencing.

B. Identification of shRNAs Inducing NFKB Response in HeLa/NFKB-GFP Reporter Cell Line, In Vitro and In Vivo.

For these experiments, a reporter cell line was used which carries the fluorescent protein GFP gene under the control of a NFKB-dependent promoter. This cell line expresses GFP upon NFKB signaling pathway activation.

1. In Vitro Experiment

Day 1.

Cells were trypsinized and resuspended to a density of $1\times10^5$ cells/ml in D-MEM supplemented with 10% FBS and 5 µg/ml Polybrene. 25 ml of cells were aliquoted to each one of twelve 15-cm plate (four plates per replicate, 10,000,000 cells per replicate, three replicates), and enough virus was added to achieve about 5,000,000 infected cells/experimental replicate. Cells were returned to $CO_2$ incubator and grown under standard conditions overnight.

Day 2.

18 h hours post-transduction, media containing virus/Polybrene was replaced with fresh media (without Polybrene).

Day 5.

96 h hours post-transduction, samples were sorted by FACS and the 5% brightest cells (GFP+) were collected.

Genomic DNA was then extracted and purified from the GFP+ sorted samples. Dual bar-codes were amplified from the entire amount of isolated genomic DNA and enumerated by HT sequencing.

2. In Vivo Experiment

Day 1.

Cells were trypsinized and resuspended to a density of $1\times10^5$ cells/ml in D-MEM supplemented with 10% FBS and 5 µg/ml Polybrene. 25 ml of cells were aliquoted to each one of twelve 15-cm plate (four plates per replicate, 10,000,000 cells per replicate, three replicates), and enough virus was added to achieve about 5,000,000 infected cells/experimental replicate. Cells were returned to $CO_2$ incubator and grown under standard conditions overnight.

Day 2.

At 16 hours post-transduction, cells were trypsinized and injected subcutaneously in immune-deficient mice (one replicate/mouse, about 6,000,000 cells/injection, two injections/mouse)

Week 3.

3 weeks after injection, developed tumors were harvested. Cells were gently dissociated by mechanical and enzymatic methods, sorted by FACS and the 5% brightest cells (GFP+) were collected.

Genomic DNA was then extracted and purified from the GFP+ sorted samples. Dual bar-codes were amplified from the entire amount of isolated genomic DNA and enumerated by HT sequencing.

Figure 8:
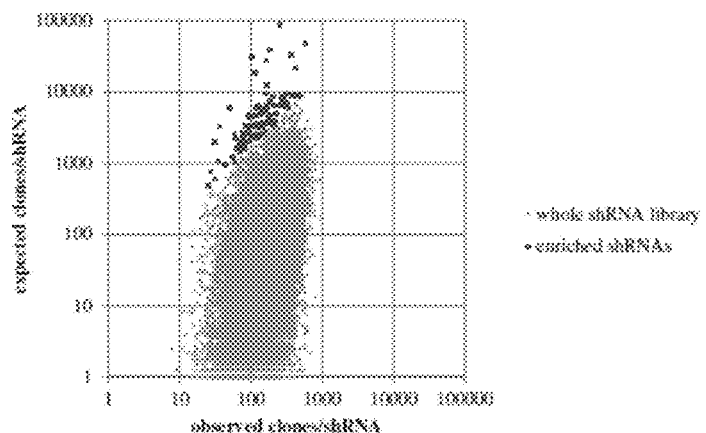
FIG. 8 provides a plot of the results of a positive selection screen reported in the Experimental section below.

3. Data Analysis of Positive Selection Screens:

The clonal analysis approach was used for the identification of shRNAs which were statistically significantly enriched from independent transductions of a pooled shRNA double-barcoded library. Enriched shRNAs were identified by comparing the number of detectable clones after selection to the relative abundance of each shRNA sequence in the shRNA plasmid library. A plot of the results is provided in FIG. 8.

IV. Additional Data

Figure 9A:
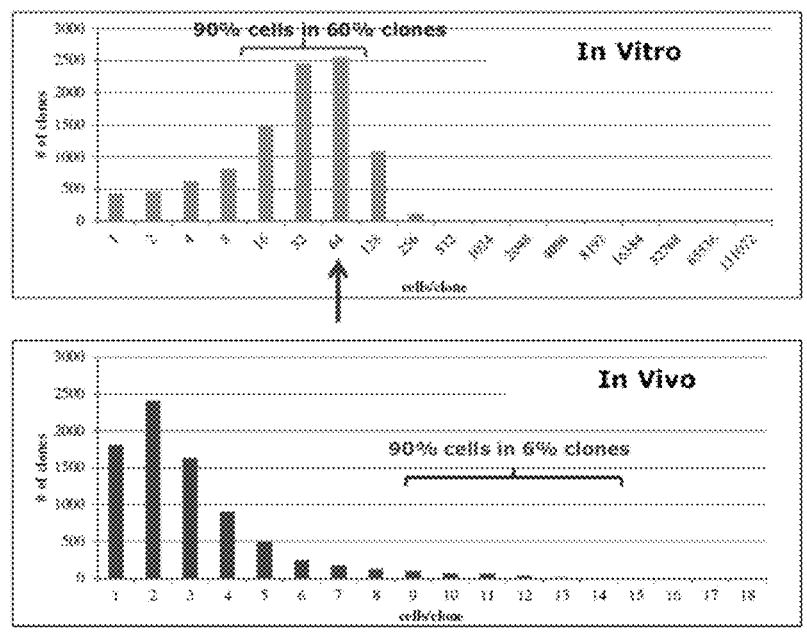

Clonal distribution (10,000 barcodes) is shown in FIG. 9A. Cells were transduced with a lentiviral library where each construct has a different barcode sequence (complex barcode library). Cells were either grown ca. 2 weeks in vitro or injected next day and grown as xenograft tumor. Barcode sequencing of total genomic DNA was performed. FIG. 9A shows the distribution of populations with each barcode (i.e., the size of each clonal population resulting from a single infection). For example (arrow), in vitro, there are slightly over 2,500 barcodes with cell populations that are ca. 64× the single cells. This means about 2,500 cells (about ¼) of the original cells doubled 6 times. In vitro, most of the cells doubled 5-7 times. In vivo, most cells did not grow or doubled a few times. About 6% of original cells proliferated exceptionally well. Long trailing distribution of clonal growth.

Figure 9B:
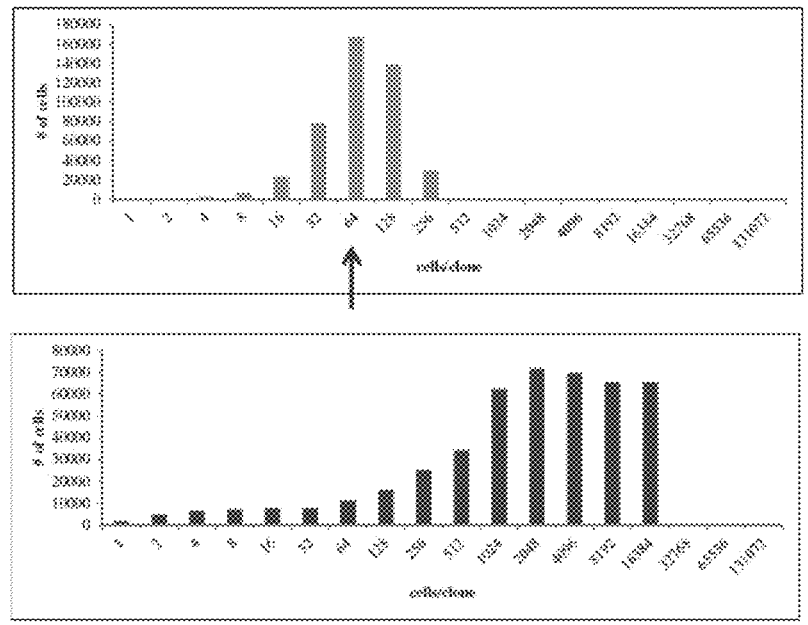

Cell distribution is shown in FIG. 9B, where the graphs show the aggregate cell number of all the clones in each population distribution. For example, in vitro, all 2500 clonal populations with 6 doublings produced ca. 17,000 cells. In vitro: Almost all of the cells were generated from the clones that doubled 5-8 times. Since cell counts align well with clonal population doublings, the total cell count is a good measure of the growth rate of the cell population with a specific shRNA. In vivo: Almost all cells in the population were generated from just the few clones that grew very well—a trailing tail. Total cell numbers only correlate with the few clones that proliferate well—these dominate the whole population.

Figure 9C:
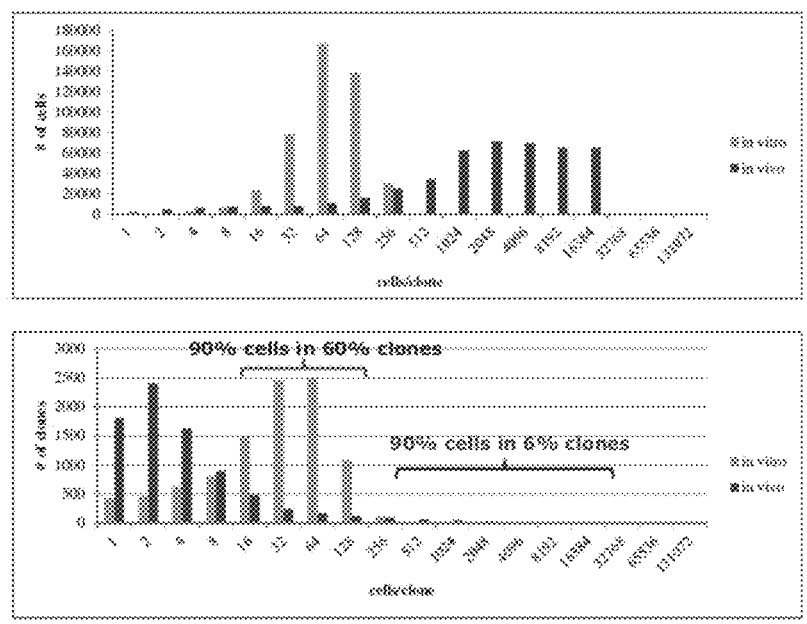

FIG. 9C shows the in vivo distribution versus the in vitro distribution of cell counts (top) and clone counts (bottom). In vitro: Most cells have roughly equivalent growth rates. For shRNA screening, the total number of cells with an shRNA accurately reflects the growth rates of all the cells that were transduced with that shRNA. In vivo: Total cell numbers only correlate with the growth rates of the few clones that dominate the whole population. Progeny of these few clones make up 90% of the cells in the population. Thus, for an shRNA screen, the shRNA counts will only tell you if one of the cells with that shRNA succeeded as one of the select group of dominate clones in the tumor. This small unrepresentative population will generate a very high degree of randomization between replicates.

Figure 9D:
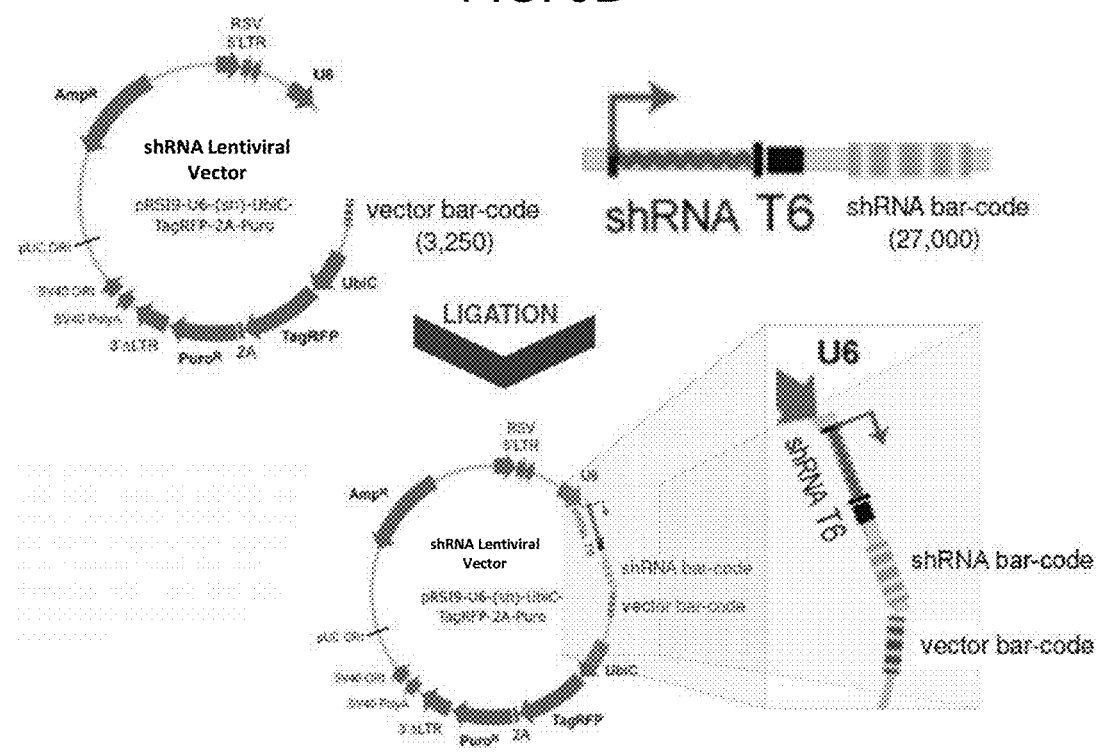

As shown in FIG. 9D, to track the growth rates of each clone transduced with a specific shRNA, a modified shRNA library was constructed where each vector-insert ligation produces a construct with its own unique barcode, with a part that still uniquely identifies the particular shRNA sequence.

An example screening approach with double barcode libraries is shown in FIG. 9E. Each transduction produces a cell with a unique barcode. In this example, the library includes more than a million (e.g., 87.75 million) unique effector constructs, which may be used to transduce, e.g., 1 million cells. The transduction may generate, e.g., about 40 clones for each shRNA, where each clone has its own barcode. The transduced cells may be expanded (e.g., for 8 doubling resulting in 250 million cells) to generate clonal populations, where each clonal population has its own barcode. Nucleic acids may be isolated and sequenced, e.g., to produce 100 million reads (100 reads per clone on average (100M/1M); 40 clones per shRNA (1M/27,000)).

Figure 9G:
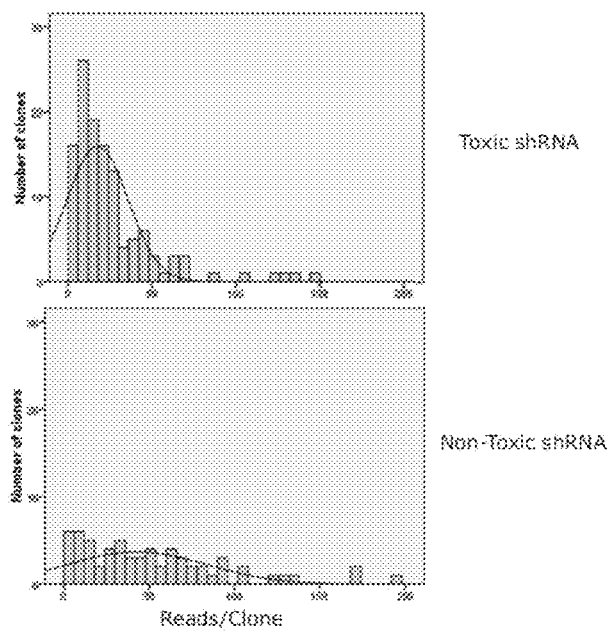

FIG. 9F shows results from an in vitro double barcode screen in triplicate. In panel (i), each graph shows the distribution of clonal populations derived from ca. 40-70 transductions of the same shRNA in a pooled screen. The top three biological replicates show the clonal distribution of a toxic shRNA in the library. Most clones do not grow or just double 1-2 times. However, a few are unaffected by the shRNA. The distribution is weighted toward the origin. The lower three graphs of panel (i) show clones containing a non-toxic shRNA in the same library screen. Some clones don't grow but most clonal populations double several times to produce a broad distribution. Panel (ii) shows the distribution of clone size and clone frequency for EIF3A (top) and luc (bottom). FIG. 9G shows the clone distribution, with the average of the three biological replicates from FIG. 9F.

Figure 9H:
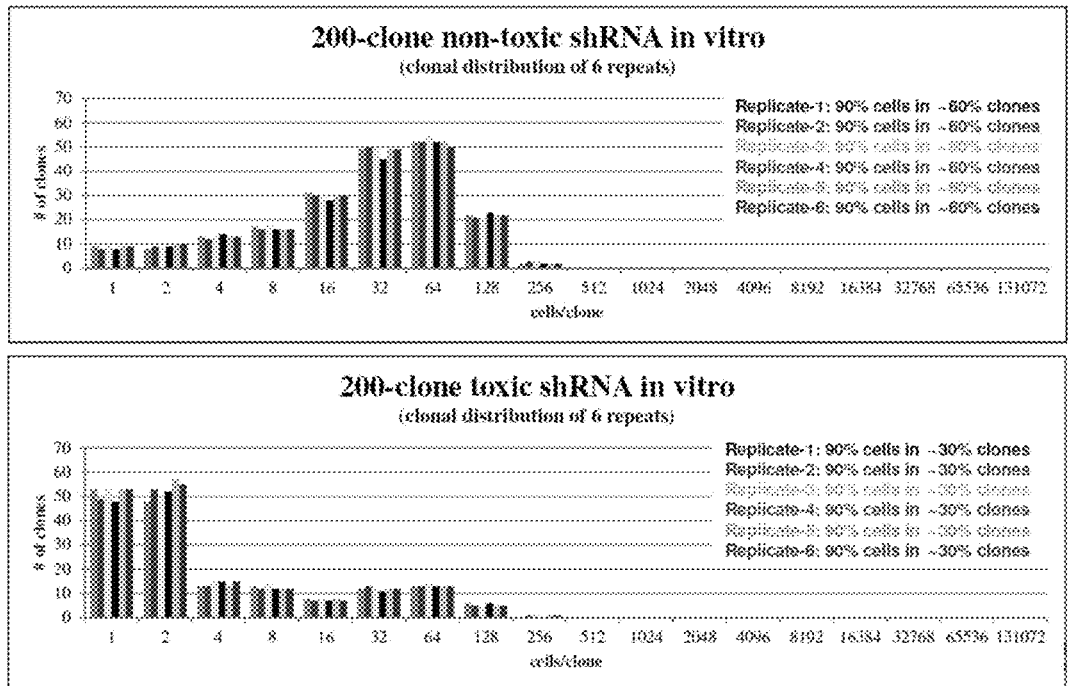

An in vitro comparison of toxic versus non-toxic clonals is shown in FIG. 9H. Distribution (normalized to 200 cells) of a non-toxic vs. a toxic shRNA from the an in vitro viability screen. With non-toxic shRNA, most clones grow and produce most of the cells. The growth distribution is relatively uniform between clones so general growth or inhibition of most of the clones directly produces higher or lower numbers of cells, which are quantified by total shRNA counts.

Figure 9I:
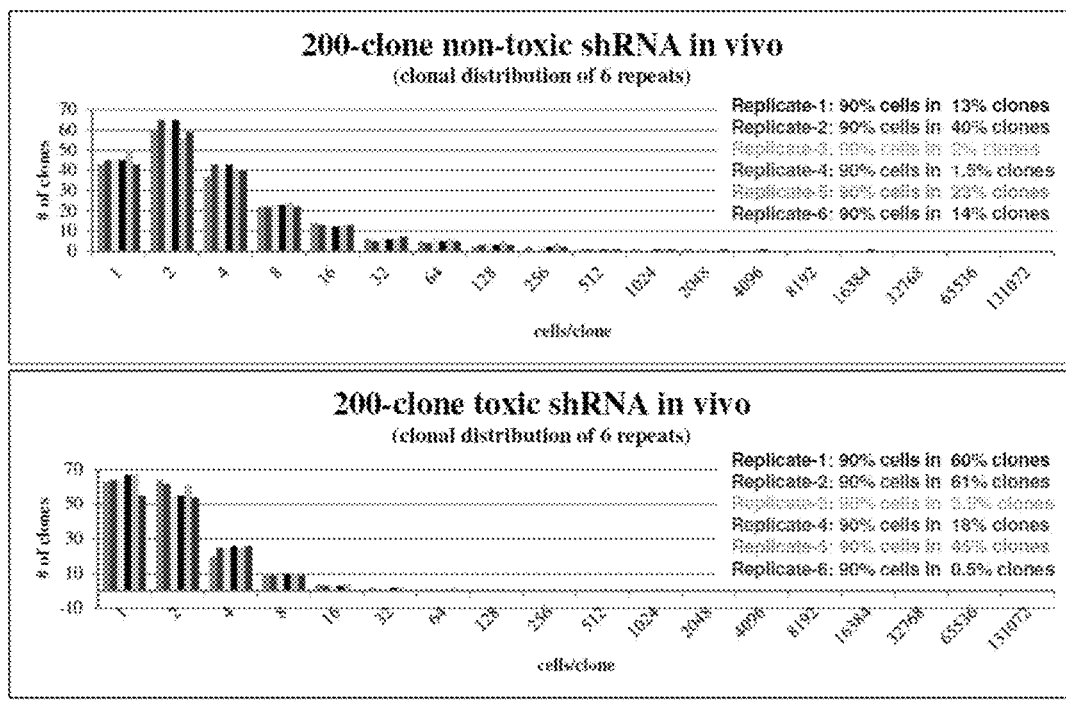

An in vivo comparison of toxic versus non-toxic clonals is shown in FIG. 9I. Calculated distribution of a non-toxic vs. a toxic shRNA in an in vivo viability screen using typical replicate variations and distributions from previous in vivo barcode cell tracking data. The difference between toxic and non-toxic shRNAs is evident by looking at the proliferation rates of all the clonal populations with an shRNA. However, since clonal growth is so disperse, almost all cells are produced by just a few very highly proliferative clones (clonal dominance). This occurs even with toxic shRNAs since growth inhibition is not uniform across all cells. Thus, cell numbers, and therefore shRNA counts, of both toxic and non-toxic shRNAs are highly variable.

Figure 9J:
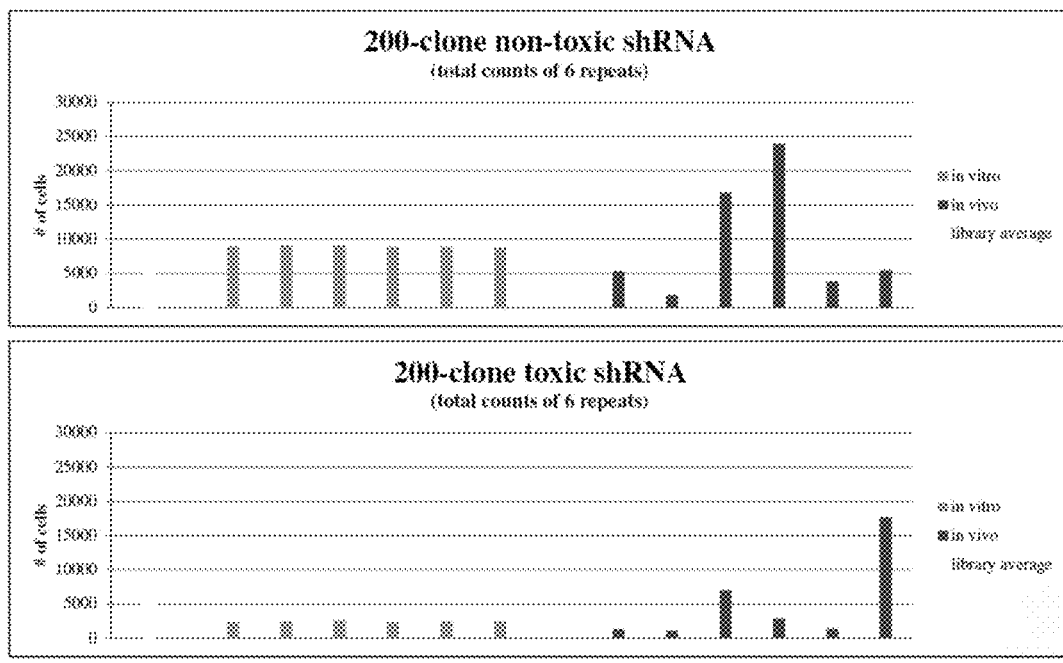

FIG. 9J shows total cells/shRNA in vitro versus in vivo. Each bar shows the total number of cells from all the clones in each scenario shown in the previous two slides. The total number of cells with the toxic or non-toxic shRNA in vitro is consistent. However, in a tumor, the total number of cells with a specific shRNA varies greatly. With sufficient replicates, it may be possible to determine some statistical difference between the number of cells with a toxic vs. a non-toxic shRNA. However, with such high variability, it is hard to assess how many replicates would be required to confidently determine this difference with even the most effective shRNA. The in vivo noise is so high the signal is difficult to discern, and replicates are more difficult than in vitro.

Problems with in vivo standard pooled screens include: (1) In vivo growth of implanted xenografts is characterized by "clonal dominance," where most of the tumor is made by the progeny of just a few implanted cells, and growth heterogeneity far exceeds the growth effects caused by shRNAs; (2) small numbers of shRNA dominate in a very dispersed background, with the rest of the shRNA counts being noisy; (3) not even the most cytotoxic shRNA fully blocks growth of all clones; (4) one dominant clone carrying a mutated or low-expressing integrant for a cytotoxic shRNA can mask a growth-inhibitory effect on all remaining clones with that shRNA; and (5) representation of each shRNA barcode varies depending on which clones dominate in a replicate so shRNA counts from in vivo replicates are inconsistent with excessive variability. A solution to the above-described problems is to assay growth rates of each cell transduced by an specific shRNA. The growth rates of clones after injection with shRNA can be tracked, and the clonal doubling rates of cells with specific shRNA can be compared.

A solution to the problems of in vivo pooled shRNA screens is as follows. Track independently transduced single shRNA sequences using a double barcoding system where one part of the barcode indicates the shRNA sequence and the other part differentiates cell clones. The double barcode screens still provide all the information available from standard genetic screens. The clonal portion of the barcode may be ignored. Screening with clonal barcodes provides two additional metrics: (1) the number of clones in the tumor with a specific shRNA; and (2) the size of each clonal population expressing a specific shRNA. Each clonal population equals one assay of how a specific shRNA affects growth so each tumor provide multiple growth assays for each shRNA. Growth rates of multiple clonal populations for each shRNA barcode provide a direct measurement of the shRNAs effect on multiple cells.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An effector construct subset of a packaged viral effector library, the effector construct subset comprising a plurality of effector constructs each comprising a common effector cassette linked to a distinct clonal barcode.

2. The effector construct subset according to claim 1, wherein the plurality of effector constructs comprises 10 or more constructs having distinct clonal barcodes.

3. The effector construct subset according to claim 2, wherein each effector construct subset comprises 100 or more distinct effector constructs each comprising a distinct clonal barcode.

4. The effector construct subset according to claim 1, wherein the effector cassette is configured to modulate the function of at least one protein selected from group consisting of CDKN2A; PTEN; EGFR; TP53; PIK3CA; RB1; NF1; MET; CDK4; ATM; PDGFRA; MDM2; APC; EP300; ERCC2; KRAS; PIK3CG; BRCA1; STK11; BRCA2; ERBB2; BRAF; FBXW7; MLH1; MSH2; SMAD4; CDKN2B; FGFR3; MSH6; PIK3CB; PIK3R1; ERCC3; JAK2; KIT; RET; AKT1; PLCG1; SMARCA4; CDH1; CDKN1A; DNMT1; ERBB3; NOTCH1; CCND2; MYC; NRAS; AKT2; CREBBP; NF2; NTRK1; PDGFRB; ABL1; CCND1; CDK6; HSP90AA1; TCF3; CTNNB1; FGFR1; FIGF; HRAS; NTRK3; WT1; CDC42; EXT1; FOXO3; MDM4; PDGFA; PMS2; RUNX1; VHL; WRN; ALK; AR; CDKN2C; CHEK1; CHEK2; ERCC5; FAS; FGFR2; HDAC1; KDR; NOS3; PTCH1; TERT; TSC2; BLM; CBL; COL1A1; EVI1; MAP2K4; PDGFB; SEPT9; TGFBR2; TRRAP; EGF; FLT3; GRB2; NCAM1; NOS2; BUB1B; CDKN1B; DIRAS3; DOT1L; EPHB1; EPHB6; GNAS; HIF1A; MRE11A; PLCG2; PRKDC; PTPN11; RAD50; RAD51; SPRY2; FANCA; FANCF; FGFR4; FLT1; FOXO1; MAP2K1; PPP2R1A; PTGS2; SHC1; TPO; XPA; XPC; BAI3; BARD1; BCL2; CARM1; CDK2; CERK; DGKZ; E2F1; EPHA3; EPO; ERBB4; FANCE; FH; FLT4; IRS1; MAPK1; NBN; PLCB1; PRKCZ; SMARCB1; TCF12; TPR; VEGFA; ABCC3; CD44; CDKN2D; CSF1R; DPYD; ESR2; EWSR1; FANCD2; FOS; LMO2; NOTCH3; PARP1; PRKCA; SMAD2; SMAD3; TSC1; ADCY9; AGAP2; BAX; BCL11A; BCR; BIRC5; CAV1; CCNE1; DGKB; EPHB4; ERCC6; ESR1; ETV1; FLNC; FN1; GSK3B; HDAC2; HOXA9; MEN1; MYH9; NCOA2; PCNA; PML; PPARG; PPARGC1A; RARA; SKP2; SOCS1; SOS1; SRC; TEK; TOP2A; TPM3; ABCA1; APC2; AURKA; CCND3; CD40LG; CDX2; CEBPA; CYP19A1; DNMT3B; ERCC1; ERCC4; ETV4; FES; GAB1; HGF; IFNG; IGF2R; INSR; KLF6; MPL; MUTYH; MYCL1; NR3C1; PIK3C3; PIK3CD; PIK3R2; PPP1R3A; PPP2R1B; PTPRB; RECQL4; ROS1; RPS6KA2; SDHB; SP1; THBS1; TP73; ANAPC5; ATR; BCL3; BIRC6; BRIP1; CBFA2T3; CDC73; CDK7; CLTC; CSMD3; CSNK1 G2; CTNNA1; CYP1B1; DDB2; DGKI; ELOVL2; EP4001; EPHA8; EPHB2; ERG; EXT2; FANCC; FANCG; FRAP1; GATA1; GMPS; GPC3; HDAC4; HIPK2; HMGA1; HOXD11; IDH1; IGF1R; IGFBP3; KALRN; KAT2B; LAMA1; LAMP1; LDHA; LTBP1; MAPK3; MAPK8IP2; MINPP1; MLL; MLL3; MST1R; MUC1; MYST4; NAV3; NOTCH2; NSD1; PAFAH1B2; PAK7; PARP2; PIGS; POLE; PPP1R13L; PPP2CB; PPP2R2B; PTCH2; PTK2; PTPRD; RAD51 L1; RHEB; RHOA; RPS6KA1; RPS6KB1; RUNX1 T1; SDHC; SDHD; SNCG; SOCS2; SPEN; TFE3; TGFBR1; TLX1; TNK2; and ZNF331.

5. The effector construct subset according to claim 1, wherein the effector cassette is selected from group consisting of a shRNA, siRNA, micro RNA, antisense RNA, ribozyme, non-coding RNA, small RNA, decoy RNA, antimir RNA, bioactive peptide, protein domain and protein effector cassette.

6. The effector construct subset according to claim 1, wherein the packaged viral effector library is a retroviral, lentiviral, adenoviral or adeno-associated viral vector library.

7. The effector construct subset according to claim 1, wherein the common effector cassette comprises an effector barcode.

8. The effector construct subset according to claim 1, wherein the common effector cassette comprises an operationally-linked promoter which is sufficient to provide expression in transduced cells.

9. The effector construct subset according to claim 1, wherein the effector constructs comprise a reporter and/or drug selection marker coding sequence that is operationally linked to a promoter.

10. A packaged viral effector library comprising a plurality of effector construct subsets, wherein each effector construct subset of the library comprises a plurality of effector constructs comprising a common effector cassette each linked to a distinct clonal barcode.

11. The packaged viral effector library according to claim 10, wherein each effector cassette comprises a unique effector barcode.

12. The packaged effector library according to claim 10, wherein each effector cassette comprises an operationally-linked promoter which is sufficient to provide expression of the effector in transduced cells.

13. The packaged effector library according to claim 12, wherein each effector construct comprises a reporter and/or drug selection marker coding sequence that is operationally linked to a promoter.

14. The packaged effector library according to claim 10, wherein the effector library comprises five or more unique effector construct subsets.

15. The packaged effector library according to claim 14, wherein each effector construct subset comprises 100 or more distinct effector constructs each comprising a distinct clonal barcode.

16. The packaged effector library according to claim 10, wherein the effector cassette is an RNAi effector cassette.

17. The packaged effector library according to claim 16, wherein the RNAi effector cassette is selected from the group consisting of a shRNA, siRNA or microRNA effector cassette.

18. The packaged effector library according to claim 10, wherein the effector cassette is an antisense RNA, ribozyme, non-coding RNA, small RNA, decoy RNA, or anti-mir RNA effector cassette.

19. The packaged effector library according to claim 10, wherein the effector cassette is a bioactive peptide, protein domain or protein effector cassette.

20. The packaged effector library according to claim 10, wherein the packaged viral effector library is a retroviral, lentiviral, adenoviral, or adeno-associated viral vector library.

21. A population of transduced target cells comprising cells transduced with a packaged viral effector library according to claim 10.

* * * * *

SEQUENCE LISTING

<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 1
aacgaactaa cgatcgtctc gacc                                    24

<210> SEQ ID NO 2
<211> LENGTH: 65
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (40)..(52)
<223> OTHER INFORMATION: n is a, c, g, or t

<400> SEQUENCE: 2
atcgtctcga ccggagtctt cttttttgaa gacacttcgn nnnnnnnnnn nnttcgtgag    60
acggt                                                                65

<210> SEQ ID NO 3
<211> LENGTH: 24
<212> TYPE: DNA
<213> ORGANISM: Artificial sequence

```
<220> FEATURE:
<223> OTHER INFORMATION: Synthetic nucleotide

<400> SEQUENCE: 3
aagcactctg ccacatagca acca                                          24

<210> SEQ ID NO 4
<211> LENGTH: 217
<212> TYPE: DNA
<213> ORGANISM: Artificial sequence
<220> FEATURE:
<223> OTHER INFORMATION: Synthetic nucleotide

<400> SEQUENCE: 4
atgattcctt catatttgca tatacgatac aaggctgtta gagagataat tggaattaat    60
ttgactgtaa acacaaagat attagtacaa aatacgtgac gtagaaagta ataaaccgga   120
gtcttctttt tgaagacac ttcgttcgga ctgtagaact ctgaacctct cggtggtcgc    180
cgtatcatta gaattctcga cctcgagaca aatggca                            217

<210> SEQ ID NO 5
<211> LENGTH: 217
<212> TYPE: DNA
<213> ORGANISM: Artificial sequence
<220> FEATURE:
<223> OTHER INFORMATION: Synthetic nucleotide

<400> SEQUENCE: 5
tactaaggaa gtataaacgt atatgctatg ttccgacaat ctctctatta accttaatta    60
aactgacatt tgtgtttcta taatcatgtt ttatgcactg catctttcat tatttggcca   120
cagaagaaaa aacttctgtg aagcaagcct gacatcttga gacttggaga gccaccagcg   180
gcatagtaat cttaagagct ggagctctgt ttaccgt                            217

<210> SEQ ID NO 6
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 6
acaaggctgt tagagagata attgga                                        26

<210> SEQ ID NO 7
<211> LENGTH: 48
<212> TYPE: DNA
<213> ORGANISM: Artificial sequence
<220> FEATURE:
<223> OTHER INFORMATION: Synthetic nucleotide

<400> SEQUENCE: 7
caagcagaag acggcatacg agattagtac aaaatacgtg acgtagaa                48

<210> SEQ ID NO 8
<211> LENGTH: 231
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (145)..(158)
<223> OTHER INFORMATION: n is a, c, g, or t
```

<400> SEQUENCE: 8

```
atgattcctt catatttgca tatacgatac aaggctgtta gagagataat tggaattaat    60
ttgactgtaa acacaaagat attagtacaa aatacgtgac gtagaaagta ataaaccgga   120
gtcttctttt tgaagacac ttcgnnnnnn nnnnnnnntt cggactgtag aactctgaac    180
ctctcggtgg tcgccgtatc attagaattc tcgacctcga gacaaatggc a            231
```

<210> SEQ ID NO 9
<211> LENGTH: 231
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (145)..(158)
<223> OTHER INFORMATION: n is a, c, g, or t

<400> SEQUENCE: 9

```
tactaaggaa gtataaacgt atatgctatg ttccgacaat ctctctatta accttaatta    60
aactgacatt tgtgtttcta taatcatgtt ttatgcactg catctttcat tatttggcca   120
cagaagaaaa aacttctgtg aagcnnnnnn nnnnnnnnaa gcctgacatc ttgagacttg   180
gagagccacc agcggcatag taatcttaag agctggagct ctgtttaccg t            231
```

<210> SEQ ID NO 10
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 10

```
aagcctgaca tcttgagact tggaga                                          26
```

<210> SEQ ID NO 11
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 11

```
aagagctgga gctctgttta ccgt                                            24
```

<210> SEQ ID NO 12
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 12

```
agagccacca gcggcatagt aa                                              22
```

<210> SEQ ID NO 13
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 13

```
agcaacaatc acagaagacg cacc                                            24
```

<210> SEQ ID NO 14
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 14
ttctctggca agcaaaagac ggcata                                          26

<210> SEQ ID NO 15
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 15
caagcagaag acggcatacg aga                                             23

<210> SEQ ID NO 16
<211> LENGTH: 136
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (105)..(122)
<223> OTHER INFORMATION: n is a, c, g, or t

<400> SEQUENCE: 16
tagaagacgc accgggatct ggattcatca agacttgtta atattcatag caagtcttgg     60
tggatccaga tcttttttgg caagcaaaag acggcatacg agatnnnnnn nnnnnnnnnn    120
nnttcgccgt cttcgt                                                    136

<210> SEQ ID NO 17
<211> LENGTH: 117
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (31)..(44)
<223> OTHER INFORMATION: n is a, c, g, or t

<400> SEQUENCE: 17
accggagtct tcttttttga agacacttcg nnnnnnnnnn nnnnttcgga ctgtagaact     60
ctgaacctct cggtggtcgc cgtatcatta gaattctcga cctcgagaca aatggca       117

<210> SEQ ID NO 18
<211> LENGTH: 117
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (31)..(44)
<223> OTHER INFORMATION: n is a, c, g, or t

<400> SEQUENCE: 18
tggccacaga agaaaaaact tctgtgaagc nnnnnnnnnn nnnnaagcct gacatcttga     60

```
gacttggaga gccaccagcg gcatagtaat cttaagagct ggagctctgt ttaccgt      117
```

<210> SEQ ID NO 19
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 19

```
aagcctgaca tcttgagact tggaga                                        26
```

<210> SEQ ID NO 20
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 20

```
aagagctgga gctctgttta ccgt                                          24
```

<210> SEQ ID NO 21
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 21

```
agagccacca gcggcatagt aa                                            22
```

<210> SEQ ID NO 22
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 22

```
ttctctggca agcaaaagac ggcata                                        26
```

<210> SEQ ID NO 23
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 23

```
caagcagaag acggcatacg aga                                           23
```

<210> SEQ ID NO 24
<211> LENGTH: 89
<212> TYPE: DNA
<213> ORGANISM: Artificial sequence
<220> FEATURE:
<223> OTHER INFORMATION: Synthetic nucleotide

<400> SEQUENCE: 24

```
accggttttt tgcaagcaa aagacggcat acgagatttc ggactgtaga actctgaacc   60
tctcggtggt cgccgtatca ttagaattc                                     89
```

<210> SEQ ID NO 25
<211> LENGTH: 89

```
<212> TYPE: DNA
<213> ORGANISM: Artificial sequence
<220> FEATURE:
<223> OTHER INFORMATION: Synthetic nucleotide

<400> SEQUENCE: 25
tggccaaaaa accgttcgtt ttctgccgta tgctctaaag cctgacatct tgagacttgg      60
agagccacca gcggcatagt aatcttaag                                        89

<210> SEQ ID NO 26
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 26
aagcctgaca tcttgagact tggaga                                           26

<210> SEQ ID NO 27
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 27
agagccacca gcggcatagt aa                                               22
```